US006599717B1

(12) United States Patent
Ebens, Jr. et al.

(10) Patent No.: US 6,599,717 B1
(45) Date of Patent: Jul. 29, 2003

(54) INVERTEBRATE VASCULAR ENDOTHELIAL GROWTH FACTOR RECEPTOR

(75) Inventors: Allen James Ebens, Jr., San Francisco, CA (US); R. Glenn Hammonds, Berkeley, CA (US); Jonathan C. Heller, San Francisco, CA (US); Greg Weddell, Vallejo, CA (US); John W. Winslow, El Granada, CA (US)

(73) Assignee: Exelixis, Inc., South San Francisco, CA (US)

( * ) Notice: Subject to any disclaimer, the term of this patent is extended or adjusted under 35 U.S.C. 154(b) by 6 days.

(21) Appl. No.: 09/677,046

(22) Filed: Sep. 29, 2000

Related U.S. Application Data

(60) Provisional application No. 60/157,355, filed on Oct. 1, 1999.

(51) Int. Cl.[7] .......................... C07K 14/71; C12N 5/10; C12N 15/12

(52) U.S. Cl. .................... 435/69.1; 536/23.1; 536/23.5; 530/350; 435/320.1; 435/325; 435/348; 435/252.3; 435/254.11

(58) Field of Search ............................... 536/23.1, 23.5, 536/23.4; 530/300, 350; 435/320.1, 69.1, 325, 252.3, 254.11, 348

(56) References Cited

U.S. PATENT DOCUMENTS 6,011,003 A * 1/2000 Charnock-Jones et al.

FOREIGN PATENT DOCUMENTS

WO WO 9533772 A1 * 12/1995

OTHER PUBLICATIONS

Adams et al., The genome sequence of *Drosophila melanogaster*, Science (Mar. 24, 2000), 287(5461):2185–2195.*

Achen et al., Vascular endothelial growth factor D (VEGF–D) is a ligand for the tyrosine kinases VEGF receptor 2(Flkl) and VEGF receptor 3 (Flt4), Proc. Natl. Acad. Sci. USA 95(2):548–553 (Jan. 20, 1998).*

Fournier et al., Interaction with the phosphotyrosine binding domain/phosphotyrosine interacting domain of SHC is required for the transforming activity of FLT4/VEGFR3 receptor tyrosine kinase, J. Biol. Chem. 271(22): 12956–12963 (May 31, 1996).*

Sawano et al., Flt–1 but not KDR/Flk–1 tyrosine kinase is a receptor for placental growth factor, which is related to vascular endothelial growth factor, Cell Growth Diff. 7:213–221 (Feb. 1996).*

Celniker,S.E., "*Drosophila melanogaster* DNA sequence (P1s DS03465 (D149) and DS08544 (D187)), complete sequence", Genbank GI No. 3041826, Sep. 15, 1998.

Kopczynski,C., et al., "CK02679.3prime CK *Drosophila melanogaster* embryo BlueScript *Drosophila melanogaster* cDNA clone CK02679 3prime, mRNA sequence", Genbank GI No. 1705364, Nov. 29, 1998.

Kopczynski,C., et al., "CK02679.5prime CK *Drosophila melanogaster* embryo BlueScript *Drosophila melanogaster* cDNA clone CK02679 5prime, mRNA sequence", Genbank GI No. 1705362, Nov. 29, 1998.

Harvey,D., et al., "SD05757.5prime SD *Drosophila melanogaster* Schneider L2 cell culture pOT2 *Drosophila melanogaster* cDNA clone SD05757 5prime, mRNA sequence", Genbank GI No. 4447930, Apr. 19, 2001.

Finnerty,H., et al., "Mus musculus receptor tyrosine kinase (FLT) mRNA, complete cds", Genbank GI No. 293782, Aug. 9, 1993.

Yamane,A., et al., "Fit–1 tyrosine kinase receptor—rat", Genbank GI No. 2143726, Sep. 24, 1999.

Shibuya,M., "Fit–1 tyrosine kinase receptor [Rattus norvegicus]", Genbank GI No. 600379, Feb. 7, 1999.

Finnerty,H., et al., "receptor tyrosine kinase—mouse", Genbank GI No. 2137724, Sep. 24, 1999.

Finnerty,H., et al., "receptor tyrosine kinase", Genbank GI No. 293783, Aug. 9, 1993.

Finnerty,H., et al., "flt–1 [Mus musculus]", Genbank GI No. 2809069, Apr. 14, 2000.

* cited by examiner

*Primary Examiner*—Lorraine Spector
*Assistant Examiner*—Claire M. Kaufman
(74) *Attorney, Agent, or Firm*—Laleh Shayesteh; Jan P. Brunelle

(57) ABSTRACT

Vascular Endothelial Growth Factor Receptor (dmVEGFR) nucleic acids and proteins that have been isolated from *Drosophila melanogaster* are described. The dmVEGFR nucleic acids and proteins can be used to genetically modify metazoan invertebrate organisms, such as insects and worms, or cultured cells, resulting in dmVEGPR expression or mis-expression. The genetically modified organisms or cells can be used in screening assays to identify candidate compounds which are potential therapeutics that interact with dmVEGFR protein. They can also be used in methods for studying dmVEGFR activity and identifying other genes that modulate the function of, or interact with, the dmVEGFR gene.

5 Claims, No Drawings

INVERTEBRATE VASCULAR ENDOTHELIAL GROWTH FACTOR RECEPTOR

RELATED APPLICATIONS

This application claims priority to provisional application No. 60/157,355, filed Oct. 1, 1999.

BACKGROUND OF THE INVENTION

The present invention relates to newly identified vascular endothelial growth factor receptor polynucleotides, their encoded polypeptides, and uses and production of such polynucleotides and polypeptides.

Formation of new blood vessels occurs as a result of two processes: vasculogenesis, which is the formation of blood vessels from progenitor cells, and angiogenesis, which is the formation of new blood vessels from preexisting vessels. Vascular endothelial growth factor (VEGF) is a secreted glycoprotein that induces angiogenesis and plays a central role in the regulation of vasculogenesis. It is highly specific for vascular endothelial cells (Dvorak et al., Am. J. Pathol. (1995) 146:1029–1039). VEGF is also known as vascular permeability factor (VPF) because of its permeabilizing effect on blood vessels. In addition to its role in the development of the vascular system, VEGF has been found to be involved in the differentiation of endothelial cells (Carmeliet et al., Nature (1996) 380:435–439; Ferrara et al., Nature, (1996) 380:439–442), cell migration, and apoptosis inhibition.

Deregulated VEGF expression contributes to the development of solid tumors by promoting tumor angiogenesis (Folkman, Nature Med. (1995) 1:27–31) and to the etiology of several additional diseases that are characterized by abnormal angiogenesis, such as metastasis, diabetic retinopathy, rheumatoid arthritis (Ferrera, Breast Cancer Res. Treat. (1995) 127–137), and abnormal wound healing (Brown et al., J. Exp. Med. (1992) 176:1375–1379).

Antibodies against VEGF can suppress tumor growth in vivo (Kim et al., Nature (1993) 362:841–844), indicating that VEGF antagonists could have broad therapeutic applications. VEGF molecules bind tyrosine kinase receptors known as VEGF receptors (VEGFRs). Three high affinity VEGFRs have been characterized in vertebrates, all of which are mainly expressed in vascular endothelial cells: VEGFR-1/FLT-1 (Yoshida et al., Cytogenet. Cell Genet. (1987) 46:724; Fong et al., Nature (1995) 376:65–69), VEGFR-2/KDR/FLK-1 (Terman et al., Oncogene (1991) 6:1677–1683; Matthews etal., Proc. Nat. Acad. Sci., (1991) 88:9026–9030), and VEGFR-3/FLT4 (Alitalo et al., U.S. Pat. No. 5,776,755; Joukov et al., EMBO J., (1996) 15:290–298). VEGFR-1, VEGFR-2, and VEGFR-3 are members of the PDGF (platelet derived growth factor) receptor family (Yarden and Ulirich, Ann. Rev. Biochem. (1988) 57: 443–478). An interesting aspect of current VEGFR biology is the perceived importance of a soluble form of VEGFR (sVEGFR), the extracellular domain without the transmembrane or intracellular domain, as an antagonist of VEGF action.

Members of signaling pathways are used reiteratively throughout evolution. For example, members of the Fibroblast Growth Factor (FGF) pathway are used in the same manner and for the same purpose, namely patterning branching morphogenesis of the respiratory system, by both insects and mammals (Metzger R J, and Krasnow M A, Science (1999) 284:1635–1639). There is a growing body of information regarding the modular subunits and the high-resolution structure of VEGF family members. Several different VEGF genes and their receptors have been identified in vertebrates. Genes from *Caenorhabditis elegans* encoding tyrosine kinase receptors sharing structural features with mammalian VEGFRs have been reported (Popovici et al., 1999 International Worm meeting abstract 680).

There is a clear need for a better understanding of the genetic pathways that VEGF gene family members are involved in. Further knowledge of the genetic pathways that involve or interact with VEGF as well as interacting pathway members and their collective functions and dysfunctions, could be used to develop therapeutics specifically targeted to the disease. The use of invertebrate model organism genetics and related technologies can greatly facilitate the elucidation of biological pathways (Scangos, Nat. Biotechnol. (1997) 15:1220–1221; Margolis and Duyk, Nature Biotech. (1998) 16:311). Invertebrate model organisms can also be used in the screening of putative pharmaceutical agents that are specifically targeted to a gene of interest. The identification of novel VEGF or VEGFR orthologs in model organisms such as *Drosophila melanogaster* would provide tools for genetic and molecular study and validation of these molecules as potential pharmaceutical targets.

SUMMARY OF THE INVENTION

It is an object of the present invention to provide invertebrate homologs of VEGFR that can be used in genetic screening methods to characterize pathways that VEGFR may be involved in as well as other interacting genetic pathways. It is also an object of the invention to provide methods for screening compounds that interact with VEGFR such as those that may have utility as therapeutics.

These and other objects are provided by the present invention which concerns the identification and characterization of a novel VEGFR in *Drosophila melanogaster*, hereinafter referred to as "dmVEGFR". Isolated nucleic acid molecules are provided that comprise nucleic acid sequences encoding dmVEGFR proteins as well as novel fragments and derivatives thereof. Methods of using the isolated nucleic acid molecules and fragments of the invention are described, such as use of RNA interference methods that block dmVEGFR activity. Vectors and host cells comprising the dmVEGFR nucleic acid molecules are also described, as well as metazoan invertebrate organisms (e.g. insects, coelomates and pseudocoelomates) that are genetically modified to express or mis-express a dmVEGFR protein.

An important utility of the novel dmVEGFR nucleic acids and proteins is that they can be used in screening assays to identify candidate compounds which are potential therapeutics that interact with dmVEGFR proteins. Further, the extracellular domain of dmVEGFR can be used as a reagent for purification of its ligand, as a biological probe of VEGF function in model organisms, and as an antagonist to VEGFR activity in vitro and in vivo.

Screening assays typically comprise contacting a dmVEGFR protein or fragment with one or more candidate molecules, and detecting any interaction between the candidate compound and the dmVEGFR protein. The assays may comprise administering the candidate molecules to cultured host cells that have been genetically engineered to express the dmVEGFR proteins, or alternatively, administering the candidate compound to a metazoan invertebrate organism that are genetically engineered to express a dmVEGFR protein.

The genetically engineered metazoan invertebrate animals of the invention can also be used in methods for studying dmVEGFR activity. These methods typically involve detecting the phenotype caused by the expression or mis-expression of the dmVEGFR protein. The methods may additionally comprise observing a second animal that has the same genetic modification as the first animal and, additionally has a mutation in a gene of interest. Any difference between the phenotypes of the two animals identifies the gene of interest as capable of modifying the function of the gene encoding the dmVEGFR protein.

DETAILED DESCRIPTION OF THE INVENTION

The use of invertebrate model organism genetics and related technologies can greatly facilitate the elucidation of biological pathways (Scangos, Nat. Biotechnol. (1997) 15:1220–1221; Margolis and Duyk, supra). Of particular use is the insect model organism, *Drosophila melanogaster* (hereinafter referred to generally as "Drosophila"). An extensive search for Vascular Endothelial Growth Factor Receptor, hereinafter referred to as VEGFR, nucleic acids and their encoded proteins in Drosophila was conducted in an attempt to identify new and useful tools for probing the function and regulation of the VEGFR genes, and for use as targets in drug discovery.

Novel VEGFR nucleic acids and their encoded proteins, hereinafter referred to as dmVEGFR, are identified herein. The newly identified dmVEGFR nucleic acids can be used for the generation of mutant phenotypes in animal models or in living cells that can be used to study regulation of dmVEGFR, and the use of dmVEGFR as a drug target. Due to the ability to rapidly carry out large-scale, systematic genetic screens, the use of invertebrate model organisms such as Drosophila has great utility for analyzing the expression and mis-expression of dmVEGFR protein. Thus, the invention provides a superior approach for identifying other components involved in the synthesis, activity, and regulation of dmVEGFR proteins. Systematic genetic analysis of VEGFRs using invertebrate model organisms can lead to the identification and validation of pesticide targets directed to components of the VEGFR pathway. Model organisms or cultured cells that have been genetically engineered to express dmVEGFR can be used to screen candidate compounds for their ability to modulate dmVEGFR expression or activity, and thus are useful in the identification of new drug targets, therapeutic agents, diagnostics and prognostics useful in the treatment of disorders associated with receptor tyrosine kinases. Additionally, these invertebrate model organisms can be used for the identification and screening of pesticide targets directed to components of the VEGFR pathway.

The details of the conditions used for the identification and/or isolation of novel dmVEGFR nucleic acids and proteins are described in the Examples section below. Various non-limiting embodiments of the invention, applications and uses of these novel dmVEGFR genes and proteins are discussed in the following sections. The entire contents of all references, including patent applications, cited herein are incorporated by reference in their entireties for all purposes. Additionally, the citation of a reference in the preceding background section is not an admission of prior art against the claims appended hereto.

dmVEGFR Nucleic Acids

The invention relates generally to nucleic acid sequences of VEGFRs, and more particularly VEGFR nucleic acid sequences of Drosophila, and methods of using these sequences. As described in the Examples below, nucleic acid sequences (SEQ ID NOs:1, 3, 5, and 7) were isolated from Drosophila that encode a VEGFR homologue. In addition to the fragments and derivatives of SEQ ID NOs:1, 3, 5, and 7 as described in detail below, the invention includes the reverse complements thereof. Also, the subject nucleic acid sequences, derivatives and fragments thereof may be RNA molecules comprising the nucleotide sequence of SEQ ID NOs:1, 3, 5, and 7 (or derivative or fragment thereof) wherein the base U (uracil) is substituted for the base T (thymine). The DNA and RNA sequences of the invention can be single- or double-stranded. Thus, the term "isolated nucleic acid sequence", as used herein, includes the reverse complement, RNA equivalent, DNA or RNA single- or double-stranded sequences, and DNA/RNA hybrids of the sequence being described, unless otherwise indicated.

Fragments of the dmVEGFR nucleic acid sequences can be used for a variety of purposes. Interfering RNA (RNAi) fragments, particularly double-stranded (ds) RNAi, can be used to generate loss-of-function phenotypes, or to formulate biopesticides. dmVEGFR nucleic acid fragments are also useful as nucleic acid hybridization probes and replication/amplification primers. Certain "antisense" fragments, i.e. that are reverse complements of portions of the coding sequence of SEQ ID NOs:1, 3, 5, or 7 have utility in inhibiting the function of dmVEGFR proteins. The fragments are of length sufficient to specifically hybridize with the corresponding SEQ ID NOs:1, 3, 5, or 7. The fragments consist of or comprise at least 12, preferably at least 24, more preferably at least 36, and most preferably at least 96 contiguous nucleotides of SEQ ID NOs:1, 3, 5, or 7. In some cases, the fragments consist of or comprise at least 200, or more preferably at least 500 contiguous nucleotides of SEQ ID NOs:1, 3, 5, or 7. In-one preferred embodiment, the fragments of at least 12, 24, 36, 96, 200, 500, 995, or 1000 nucleotides are of any contiguous stretch of nucleotides 1 to 4040 of SEQ ID NOs:1, 3, 5, or 7. When these fragments are flanked by other nucleic acid sequences, the total length of the combined nucleic acid sequence is less than 20 kb, preferably less than 15 kb, 10 kb, or 5 kb, more preferably less than 2 kb, and in some cases, preferably less than 500 bases.

Additional preferred fragments of SEQ ID NO:1 encode domains having homology with immunoglobulin superfamily (IgSF) domains, which are located at approximately nucleotides 439–664, 820–1027, 1133–1346, 1441–1654 1748–1994, 2114–2309, and 1435–1609; extracellular domain, located at approximately nucleotides 368–2675; extracellular and transmembrane domain, located at approximately nucleotides 368–2744; and tyrosine kinase domains, located at approximately nucleotides 2906–3215, and 3620–4076.

Additional preferred fragments of SEQ ID NO:3 encode domains having homology with immunoglobulin superfamily (IgSF) domains, which are located at approximately nucleotides 228–357, 522–687, 828–1041, 1164–1338, 1443–1512, 1809–2004, and 2130–2304; extracellular domain, located at approximately nucleotides 1–2376; and tyrosine kinase domains, located at approximately nucleotides 2601–2910, and 3210–3666.

Additional preferred fragments of SEQ ID NO:5 encode domains having homology with immunoglobulin superfamily (IgSF) domains, which are located at approximately nucleotides 228–357, 522–687, 810–1023, 1146–1320, 1425–1494, 1791–1986, 2112–2286; extracellular domain, located at approximately nucleotides 1–2358; and tyrosine kinase domains, located at approximately nucleotides 2583–2892, and 3297–3753.

Additional preferred fragments of SEQ ID NO:7 encode domains having homology with immunoglobulin superfamily (IgSF) domains, which are located at approximately nucleotides 228–357, and 522–687; and extracellular domain, located at approximately nucleotides 1–759.

Other preferred fragments of SEQ ID NO:1 consist of or comprise a sequence of less than 15kb that encodes a stretch of at least 12, preferably at least 15, more preferably at least 20, and most preferably at least 25 contiguous amino acids from any of amino acids 1 to 1000 of SEQ ID NO:2 or amino acids 22 to 796 of SEQ ID NO:2. Other preferred fragments of SEQ ID NO:3 consist of or comprise a sequence of less than 15kb that encodes a stretch of at least 12, preferably at least 15, more preferably at least 20, and most preferably at least 25 contiguous amino acids from any of amino acids 1 to 1000 of SEQ ID NO:4 or amino acids 1–792 of SEQ ID NO:4.

Other preferred fragments of SEQ ID NO:5 consist of or comprise a sequence of less than 15kb that encodes a stretch of at least 12, preferably at least 15, more preferably at least 20, and most preferably at least 25 contiguous amino acids from any of amino acids 1 to 1000 of SEQ ID NO:6 or amino acids 1 to 786 of SEQ ID NO:6.

Other preferred fragments of SEQ ID NO:7 consist of or comprise a sequence of less than 15kb that encodes a stretch of at least 12, preferably at least 15, more preferably at least 20, and most preferably at least 25 contiguous amino acids from any of amino acids 1 to 253 of SEQ ID NO:8.

The subject nucleic acid sequences may consist solely of SEQ ID NOs:1, 3, 5, or 7 or fragments thereof. Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated and/or are purified, i.e. unaccompanied by at least some of the material with which it is associated in its natural state. Preferably, the isolated nucleic acids constitute at least about 0.5%, and more preferably at least about 5% by weight of the total nucleic acid present in a given fraction, and are preferably recombinant, meaning that they comprise a non-natural sequence or a natural sequence joined to nucleotide (s) other than that which it is joined to on a natural chromosome.

Derivative nucleic acid sequences of dmVEGFR include sequences that hybridize to the nucleic acid sequence of SEQ ID NO:1 under stringency conditions such that the hybridizing derivative nucleic acid is related to the subject nucleic acid by a certain degree of sequence identity. A nucleic acid molecule is "hybridizable" to another nucleic acid molecule, such as a cDNA, genomic DNA, or RNA, when a single stranded form of the nucleic acid molecule can anneal to the other nucleic acid molecule. Stringency of hybridization refers to conditions under which nucleic acids are hybridizable. The degree of stringency can be controlled by temperature, ionic strength, pH, and the presence of denaturing agents such as formamide during hybridization and washing. As used herein, the term "stringent hybridization conditions" are those normally used by one of skill in the art to establish at least a 90% sequence identity between complementary pieces of DNA or DNA and RNA. "Moderately stringent hybridization conditions" are used to find derivatives having at least 70% sequence identity. Finally, "low-stringency hybridization conditions" are used to isolate derivative nucleic acid molecules that share at least about 50% sequence identity with the subject-nucleic acid sequence.

The ultimate hybridization stringency reflects both the actual hybridization conditions as well as the washing conditions following the hybridization, and it is well known in the art how to vary the conditions to obtain the desired result. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). A preferred derivative nucleic acid is capable of hybridizing to SEQ ID NO:1 under stringent hybridization conditions that comprise: prehybridization of filters containing nucleic acid for 8 hours to overnight at 65° C. in a solution comprising 6×single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18–20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.2×SSC and 0.1% SDS (sodium dodecyl sulfate).

Derivative nucleic acid sequences that have at least about 70% sequence identity with any of SEQ ID NOs:1, 3, 5, and 7 are capable of hybridizing to SEQ ID NOs:1, 3, 5, or 7 under moderately stringent conditions that comprise: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% Ficoll, 1% BSA, and 500 μg/ml denatured salmon sperm DNA; hybridization for 18–20 h at 40° C. in a solution containing 35% formamide, 5×SSC, 50 mM Tris-HCl (pH7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS.

Other preferred derivative nucleic acid sequences are capable of hybridizing to any of SEQ ID NOs:1, 3, 5, or 7 under low stringency conditions that comprise: incubation for 8 hours to overight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

As used herein, "percent (%) nucleic acid sequence identity" with respect to a subject sequence, or a specified portion of a subject sequence, is defined as the percentage of nucleotides in the candidate derivative nucleic acid sequence identical with the nucleotides in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; hereinafter referred to generally as "BLAST") with all the search parameters set to default values. The HSP S and HSP S2 parameters are dynamic values and are established by the program itself depending upon the composition of the particular sequence and composition of the particular database against which the sequence of interest is being searched. A percent (%) nucleic acid sequence identity value is determined by the number of matching identical nucleotides divided by the sequence length for which the percent identity is being reported.

Derivative dmVEGFR nucleic acid sequences usually have at least 70% sequence identity, preferably at least 80% sequence identity, more preferably at least 85% sequence identity, still more preferably at least 90% sequence identity, and most preferably at least 95% sequence identity with any of SEQ ID NOs:1, 3, 5, and 7 or a domain-encoding region thereof. In one preferred embodiment, the derivative nucleic acid encodes a polypeptide comprising a dmVEGFR amino acid sequence of any of SEQ ID NOs:2, 4, 6, 8 or a fragment or derivative thereof as described further below under the subheading "dmVEGFR proteins". In a preferred embodiment, a derivative of any of SEQ ID NOs:1, 3, 5, and 7 consists of or comprises a sequence of less than 15kb that encodes a stretch of at least 20, preferably 22, more preferably 25, and most preferably at least 30 contiguous amino acids that share 100% sequence similarity with an equivalent number of contiguous amino acids from any of amino acids 1 to 796 of any of SEQ ID NOs:2, 4, or 6 or amino acids 1 to 253 of SEQ ID NO:8.

A derivative dmVEGFR nucleic acid sequence, or fragment thereof, may comprise 100% sequence identity with any of SEQ ID NOs:1, 3, 5, or 7 but be a derivative thereof in the sense that it has one or more modifications at the base or sugar moiety, or phosphate backbone. Examples of modifications are well known in the art (Bailey, Ullmann's Encyclopedia of Industrial Chemistry (1998), 6th ed. Wiley and Sons). Such derivatives may be used to provide modified stability or any other desired property.

Another type of derivative of the subject nucleic acid sequences includes corresponding humanized sequences. A humanized nucleic acid sequence is one in which one or more codons has been substituted with a codon that is more commonly used in human genes. Preferably, a sufficient number of codons have been substituted such that a higher level expression is achieved in mammalian cells than what would otherwise be achieved without the substitutions. The following list shows, for each amino acid, the calculated codon frequency (number in parentheses) in humans genes for 1000 codons (Wada et al., Nucleic Acids Research (1990) 18(Suppl.):2367–2411):

Human codon frequency per 1000 codons:

ARG: CGA (5.4), CGC (11.3), CGG (10.4), CGU (4.7), AGA (9.9), AGG (11.1)
LEU: CUA (6.2), CUC (19.9), CUG (42.5), CUU (10.7), UUA (5.3), UUG (11.0)
SER: UCA (9.3), UCC (17.7), UCG (4.2), UCU (13.2), AGC (18.7), AGU (9.4)
THR: ACA (14.4), ACC (23.0), ACG (6.7), ACU (12.7)
PRO: CCA (14.6), CCC (20.0), CCG (6.6), CCU (15.5)
ALA: GCA (14.0), GCC (29.1), GCG (7.2), GCU (19.6)
GLY: GGA (17.1), GGC (25.4), GGG (17.3), GGU (11.2)
VAL: GUA (5.9), GUC (16.3), GUG (30.9), GUU (10.4)
LYS: AAA (22.2), AAG (34.9)
ASN: AAC (22.6), AAU (16.6)
GLN: CAA (11.1), CAG (33.6)
HIS: CAC (14.2), CAU (9.3)
GLU: GAA (26.8), GAG (41.4)
ASP: GAC (29.0), GAU (21.7)
TYR: UAC (18.8), UAU (12.5)
CYS: UGC (14.5), UGU (9.9)
PHE: UUU (22.6), UUC (15.8)
ILE: AUA (5.8), AUC (24.3), AUU (14.9)
MET: AUG (22.3)
TRP: UGG (13.8)
TER: UAA (0.7), AUG (0.5), UGA (1.2)

Thus, a dmVEGFR nucleic acid sequence in which the glutamic acid codon, GAA has been replaced with the codon GAG, which is more commonly used in human genes, is an example of a humanized dmVEGFR nucleic acid sequence. A detailed discussion of the humanization of nucleic acid sequences is provided in U.S. Pat. No. 5,874,304 to Zolotukhin et al.

Nucleic acids encoding the amino acid sequence of any of SEQ ID NOs:2, 4, 6, or 8 or fragments or derivatives thereof, may be obtained from an appropriate cDNA library prepared from any eukaryotic species that encodes VEGFR proteins such as vertebrates, preferably mammalian (e.g. primate, porcine, bovine, feline, equine, and canine species, etc.) and invertebrates, such as arthropods, particularly insects species (preferably Drosophila), acarids, crustacea, molluscs, nematodes, and other worms. An expression library can be constructed using known methods. For example, mRNA can be isolated to make cDNA which is ligated into a suitable expression vector for expression in a host cell into which it is introduced. Various screening assays can.then be used to select for the gene or gene product (e.g. oligonucleotides of at least about 20 to 80 bases designed to identify the gene of interest, or labeled antibodies that specifically bind to the gene product). The gene and/or gene product can then be recovered from the host cell using known techniques.

Polymerase chain reaction (PCR) can also be used to isolate nucleic acids of the dmVEGFR where oligonucleotide primers representing fragmentary sequences of interest amplify RNA or DNA sequences from a source such as a genomic or cDNA library (as described by Sambrook et al., supra). Additionally, degenerate primers for amplifying homologues from any species of interest may be used. Once a PCR product of appropriate size and sequence is obtained, it may be cloned and sequenced by standard techniques, and utilized as a probe to isolate a complete cDNA or genomic clone.

Fragmentary sequences of dmVEGFR nucleic acids and derivatives may be synthesized by known methods. For example, oligonucleotides may be synthesized using an automated DNA synthesizer available from commercial suppliers (e.g. Biosearch, Novato, Calif.; Perkin-Elmer Applied Biosystems, Foster City, Calif.). Antisense RNA sequences can be produced intracellularly by transcription from an exogenous sequence, e.g. from vectors that contain antisense dmVEGFR nucleic acid sequences. Newly generated sequences may be identified and isolated using standard methods.

An isolated dmVEGFR nucleic acid sequence can be inserted into any appropriate cloning vector, for example bacteriophages such as lambda derivatives, or plasmids such as PBR322, pUC plasmid derivatives and the Bluescript vector (Stratagene, San Diego, Calif.). Recombinant molecules can be introduced into host cells via transformation, transfection, infection, electroporation, etc., or into a transgenic animal such as a fly. The transformed cells can be cultured to generate large quantities of the dmVEGFR nucleic acid. Suitable methods for isolating and producing the subject nucleic acid sequences are well-known in the art (Sambrook et al., supra; DNA Cloning: A Practical Approach, Vol. 1, 2, 3, 4, (1995) Glover, ed., MRL Press, Ltd., Oxford, U.K.).

The nucleotide sequence encoding a dmVEGFR protein or fragment or derivative thereof, can be inserted into any appropriate expression vector for the transcription and translation of the inserted protein-coding sequence. Alternatively, the necessary transcriptional and translational signals can be supplied by the native dmVEGFR gene and/or its flanking regions. A variety of host-vector systems may be utilized to express the protein-coding sequence such as mammalian cell systems infected with virus (e.g. vaccinia virus, adenoviruts, etc.); insect cell systems infected with virus (e.g. baculovirus); microorganisms such as yeast containing yeast vectors, or bacteria transformed with bacteriophage, DNA, plasmid DNA, or cosmid DNA. Expression of a dmVEGFR protein may be controlled by a suitable promoter/enhancer element. In addition, a host cell strain may be selected which modulates the expression of the inserted sequences, or modifies and processes the gene product in the specific fashion desired.

To detect expression of the dmVEGFR gene product, the expression vector can comprise a promoter operably linked to a dmVEGFR gene nucleic acid, one or more origins of replication, and, one or more selectable markers (e.g. thymidine kinase activity, resistance to antibiotics, etc.). Alternatively, recombinant expression vectors can be identified by assaying for the expression of the dmVEGFR gene product based on the physical or functional properties of the dmVEGFR protein in in vitro assay systems (e.g. immunoassays).

The dmVEGFR protein, fragment, or derivative may be optionally expressed as a fusion, or chimeric protein product (i.e. it is joined via a peptide bond to a heterologous protein sequence of a different protein). A chimeric product can be made by ligating the appropriate nucleic acid sequences encoding the desired amino acid sequences to each other in the proper coding frame using standard methods and expressing the chimeric product. A chimeric product may also be made by protein synthetic techniques, e.g. by use of a peptide synthesizer.

Once a recombinant that expresses the dmVEGFR gene sequence is identified, the gene product can be isolated and purified using standard methods (e.g. ion exchange, affinity, and gel exclusion chromatography; centrifugation; differential solubility; electrophoresis). The amino acid sequence of the protein can be deduced from the nucleotide sequence of the chimeric gene contained in the recombinant and can thus be synthesized by standard chemical methods (Hunkapiller et al., Nature (1984) 310:105–111). Alternatively, native dmVEGFR proteins can be purified from natural sources, by standard methods (e.g. immunoaffinity purification).

dmVEGFR Proteins dmVEGFR proteins of the invention comprise or consist of an amino acid sequence of SEQ ID NOs:2, 4,6, and 8 or fragments or derivatives thereof. Compositions comprising these proteins may consist essentially of the dmVEGFR protein, fragments, or derivatives, or may comprise additional components (e.g. pharmaceutically acceptable carriers or excipients, culture media, carriers used in pesticide formulations, etc.).

dmVEGFR protein derivatives typically share a certain degree of sequence identity or sequence similarity with any of SEQ ID NOs:2, 4, 6, or 8, or a fragment thereof. As used herein, "percent (%) amino acid sequence identity" with respect to a subject sequence, or a specified portion of a subject sequence, is defined as the percentage of amino acids in the candidate derivative amino acid sequence identical with the amino acid in the subject sequence (or specified portion thereof), after aligning the sequences and introducing gaps, if necessary to achieve the maximum percent sequence identity, as generated by BLAST (Altschul et al., supra) using the same parameters discussed above for derivative nucleic acid sequences. A % amino acid sequence identity value is determined by the number of matching identical amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, and glycine.

In one preferred embodiment, a dmVEGFR protein derivative shares at least 80% sequence identity or similarity, preferably at least 85%, more preferably at least 90%, and most preferably at least 95% sequence identity or similarity with a contiguous stretch of at least 20 amino acids, preferably at least 25 amino acids, more preferably at least 30 amino acids, and in some cases, the entire length of SEQ ID NOs:2, 4, 6, or 8. In a preferred embodiment, the stretch of at least 20, 25, or 30 contiguous amino acids is from any of amino acids 1 to 1000 of SEQ ID NOs:2, 4, or 6, any amino acids 22 to 796 of SEQ ID NOs:2, 4, 6, or any amino acids 1–253 of SEQ ID NO:8.

In another embodiment, the dmVEGFR protein derivative may consist of or comprise a sequence that shares 100% similarity with any contiguous stretch of at least 20 amino acids, preferably at least 22 amino acids, more preferably at least 25 amino acids, and most preferably at least 28 amino acids of any of SEQ ID NOs:2, 4, 6, and 8, or any of amino acids 1 to 1000 of SEQ ID NOs:2, 4, and 6, or any of amino acids 22 to 796 of any of SEQ ID NOs:2, 4, or 6.

Preferred derivatives of dmVEGFR consist of or comprise an amino acid sequence that has at least 70%, preferably at least 80%, more preferably at least 85%, still more preferably at least 90%, and most preferably at least 95% sequence identity or sequence similarity with any of amino acid residues 22–796, which is the likely extracellular domain; residues 22–813, the extracellular and transmembrane domains; residues 45–120, 172–241, 276–347, 379–450, 481–563, 603–668, and 709–768, the immunoglobulin homology (IgG-like) domains; residues 867–970, and 1105–1257, the tyrosine kinase domains; or the entire length of SEQ ID NO:2.

Other preferred derivatives of dmVEGFR consist of or comprise an amino acid sequence that has at least 70%, preferably at least 80%, more preferably at least 85%, still more preferably at least 90%, and most preferably at least 95% sequence identity or sequence similarity with any of amino acid residues 22–796, which is the likely extracellular domain; residues 76–119, 174–229, 276–347, 388–446, 481–504, 603–668, and 710–768, the immunoglobulin homology (IgG-like) domains; residues 867–970, and 1070–1222, the tyrosine kinase domains; or the entire length of SEQ ID NO:4.

Further preferred derivatives of dmVEGFR consist of or comprise an amino acid sequence that has at least 70%, preferably at least 80%, more preferably at least 85%, still more preferably at least 90%, and most preferably at least 95% sequence identity or sequence similarity with any of amino acid residues 22–786, which is the likely extracellular domain; residues 76–119, 174–229, 270–341, 382–440, 475–498, 597–662, and 704–762, the immunoglobulin homology (IgG-like) domains; residues 861–964, and 1099–1251, the tyrosine kinase domains; or the entire length of SEQ ID NO:6.

Still further preferred derivatives of dmVEGFR consist of or comprise an amino acid sequence that has at least 70%, preferably at least 80%, more preferably at least 85%, still more preferably at least 90%, and most preferably at least 95% sequence identity or sequence similarity with any of amino acid residues 22–253, which is the likely extracellular domain, or the entire length of SEQ ID NO:8.

Preferred fragments of dmVEGFR proteins consist or comprise at least 12, preferably at least 14, more preferably at least 17, and most preferably at least 22 contiguous amino acids of any of SEQ ID NOs:2, 4, 6, or 8, any of amino acids. 1 to 1000 of SEQ ID NOs:2, 4, or 6, any of amino acids 22 to 796 of SEQ ID NOs:2, 4, 6, or the entire length of SEQ ID NO:8. The fragment or derivative of the dmVEGFR protein is preferably "functionally active" meaning that the dmVEGFR protein derivative or fragment exhibits one or more functional activities associated with a full-length, wild-type VEGFR protein comprising the-amino acid sequence of SEQ ID NOs:2, 4, 6, or 8. As one example, a fragment or derivative may have antigenicity such that it can be used in immunoassays, for immunization, for inhibition of dmVEGFR activity, etc, as discussed further below regarding generation of antibodies to dmVEGFR proteins. Preferably, a functionally active dmVEGFR fragment or derivative is one that displays one or more biological activities associated with VEGFR proteins such as tyrosine kinase receptor activity. For purposes herein, functionally active fragments also include those fragments that exhibit one or more structural features of a VEGFR, such as the extracellular domain including the immunoglobulin homology domains, the transmembrane domain, and the intracellular domain containing the tyrosine kinase domains. The functional activity of dmVEGFR proteins, derivatives and fragments can be assayed by various methods known to one skilled in the art (Current Protocols in Protein Science (1998) Coligan et al., eds., John Wiley & Sons, Inc., Somerset, N.J.). In a preferred method, which is described in detail below, a model organism, such as Drosophila, is used in genetic studies to assess the phenotypic effect of a fragment or derivative (i.e. a mutant dmVEGFR protein).

dmVEGFR derivatives can be produced by various methods known in the art. The manipulations which result in their production can occur at the gene or protein level. For example, a cloned VEGFR gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, a VEGFR gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB® linkers (available from Pharmacia and Upjohn, Kalamazoo, Mich.), etc.

At the protein level, manipulations include post translational modification, e.g. glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.). Derivative proteins can also be chemically synthesized by use of a peptide synthesizer, for example to introduce nonclassical amino acids or chemical amino acid analogs as substitutions or additions into the dmVEGFR protein sequence.

Chimeric or fusion proteins can be made comprising a VEGFR protein or fragment thereof (preferably comprising one or more structural or functional domains of the dmVEGFR protein) joined at its amino- or carboxy-terminus via a peptide bond to an amino acid sequence of a different protein. Chimeric proteins can be produced by any known method, including: recombinant expression of a nucleic acid encoding the protein (comprising a VEGFR-coding sequence joined in-frame to a coding sequence for a different protein); ligating the appropriate nucleic acid sequences encoding the desired amino acid sequences to each other in the proper coding frame, and expressing the chimeric product; and protein synthetic techniques, e.g. by use of a peptide synthesizer.

dmVEGFR Gene Regulatory Elements dmVEGFR gene regulatory DNA elements such as enhancers or promoters that reside within nucleotides 1 to 304 of SEQ ID NO:1, can be used to identify tissues, cells, genes and factors that specifically control dmVEGFR protein production. Preferably least 20, more preferably at least 25, and most preferably at least 50 contiguous nucleotides within nucleotides 1 to 304 of SEQ ID NO:1 are used. Analyzing components that are specific to dmVEGFR protein function can lead to an understanding of how to manipulate these regulatory processes, especially for pesticide and therapeutic applications, as well as an understanding of how to diagnose dysfunction in these processes.

Gene fusions with the dmVEGFR regulatory elements can be made. For compact genes that have relatively few and small intervening sequences, such as those described herein for Drosophila, it is typically the case that the regulatory elements that control spatial and temporal expression patterns are found in the DNA immediately upstream of the coding region, extending to the nearest neighboring gene. Regulatory regions can be used to construct gene fusions where the regulatory DNAs are operably fused to a coding region for a reporter protein whose expression is easily detected, and these constructs are introduced as transgenes into the animal of choice. An entire regulatory DNA region can be used, or the regulatory region can be divided into smaller segments to identify sub-elements that might be specific for controlling expression a given cell type or stage of development. Reporter proteins that can be used for construction of these gene fusions include *E. coli* beta-galactosidase and green fluorescent protein (GFP). These can be detected readily in situ, and thus are useful for histological studies and can be used to sort cells that express dmVEGFR proteins (OKane and Gehring PNAS (1987) 84(24):9123–9127; Chalfie et al., Science (1994) 263:802–805; and Cumberledge and Krasnow (1994) Methods in Cell Biology 44:143–159). Recombinase proteins, such as FLP or Cre, can be used in controlling gene expression through site-specific recombination (Golic and Lindquist (1989) Cell 59(3):499–509; White et al., Science (1996) 271:805–807). Toxic proteins such as the reaper and hid cell death proteins, are useful to specifically ablate cells that normally express dmVEGFR proteins in order to assess the physiological function of the cells (Kingston, In Current Protocols in Molecular Biology (1998) Ausubel et al., John Wiley & Sons, Inc. sections 12.0.3–12.10) or any other protein where it is desired to examine the function this particular protein specifically in cells that synthesize dmVEGFR proteins.

Alternatively, a binary reporter system can be used, similar to that described further below, where the dmVEGFR regulatory element is operably fused to the coding region of an exogenous transcriptional activator protein, such as the GAL4 or tTA activators described below, to create a dmVEGFR regulatory element "driver gene". For the other half of the binary system the exogenous activator controls a separate "target gene" containing a coding region of a reporter protein operably fused to a cognate regulatory element for the exogenous activator protein, such as $UAS_G$ or a tTA-response element, respectively. An advantage of a binary system is that a single driver gene construct can be used to activate transcription from preconstructed target genes encoding different reporter proteins, each with its own uses as delineated above.

dmVEGFR regulatory element-reporter gene fusions are also useful for tests of genetic interactions, where the objective is to identify those genes that have a specific role in controlling the expression of dmVEGFR genes, or promoting the growth and differentiation of the tissues that expresses the dmVEGFR proteins. dmVEGFR gene regulatory DNA elements are also useful in protein-DNA binding assays to identify gene regulatory proteins that control the expression of dmVEGFR genes. The gene regulatory proteins can be detected using a variety of methods that probe specific protein-DNA interactions well known to those skilled in the art (Kingston, supra) including in vivo footprinting assays based on protection of DNA sequences from chemical and enzymatic modification within living or permeabilized cells; and in vitro footprinting assays based on protection of DNA sequences from chemical or enzymatic modification using protein extracts, nitrocellulose filter-binding assays and gel electrophoresis mobility shift assays using radioactively labeled regulatory DNA elements mixed with protein extracts. Candidate dmVEGFR gene regulatory proteins can be purified using a combination of conventional and DNA-affinity purification techniques. Molecular cloning strategies can also be used to identify proteins that specifically bind dmVEGFR gene regulatory DNA elements. For example, a Drosophila cDNA library in an expression vector, can be screened for cDNAs that encode dmVEGFR gene regulatory element DNA-binding activity. Similarly, the yeast "one-hybrid" system can be used (Li and Herskowitz, Science (1993) 262:1870–1874; Luo et al., Biotechniques (1996) 20(4):564–568; Vidal et al., PNAS (1996) 93(19):10315–10320).

Identification of Molecules that Interact with dmVEGFR

A variety of methods can be used to identify or screen for molecules, such as proteins or other molecules, that interact with dmVEGFR proteins, or derivatives or fragments thereof. The assays may employ purified dmVEGFR protein, or cell lines or model organisms such as Drosophila and *C. elegans*, that have been genetically engineered to express dmVEGFR protein. Suitable screening methodologies are well known in the art to test for proteins and oiher molecules that interact with dmVEGFR genes and proteins (see e.g. PCT International Publication No. WO 96/34099). For example, the extracellular domain of dmVEGFR can be labeled and used as a probe to isolate VEGFR ligands. The newly identified interacting molecules may provide new targets for pharmaceutical agents. Any of a variety of exogenous molecules, both naturally occurring and/or synthetic (e.g., libraries of small molecules or peptides, or phage display libraries), may be screened for binding capacity. In a typical binding experiment, the dmVEGFR protein or fragment is mixed with candidate molecules under conditions conducive to binding, sufficient time is allowed for any binding to occur, and assays are performed to test for bound complexes. Assays to find interacting proteins can be performed by any method known in the art, for example, immunoprecipitation with an antibody that binds to the protein in a complex followed by analysis by size fractionation of the immunoprecipitated proteins (e.g. by denaturing or nondenaturing polyacrylamide gel electrophoresis), Western analysis, non-denaturing gel electrophoresis, etc.

Two-hybrid Assay Systems

A preferred method for identifying interacting proteins is a two-hybrid assay system or variation thereof (Fields and Song, Nature (1989) 340:245–246; U.S. Pat. No. 5,283,173; for review see Brent and Finley, Annu. Rev. Genet. (1997) 31:663–704). The most commonly used two-hybrid screen system is performed using yeast. All systems share three elements: 1) a gene that directs the synthesis of a "bait" protein fused to a DNA binding domain; 2) one or more "reporter" genes having an upstream binding site for the bait, and 3) a gene that directs the synthesis of a "prey" protein fused to an activation domain that activates transcription of the reporter gene. For the screening of proteins that interact with dmVEGFR protein, the "bait" is preferably a dmVEGFR protein, expressed as a fusion protein to a DNA binding domain; and the "prey" protein is a protein to be tested for ability to interact with the bait, and is expressed as a fusion protein to a transcription activation domain. The prey proteins can be obtained from recombinant biological libraries expressing random peptides.

The bait fusion protein can be constructed using any suitable DNA binding domain, such as the *E. coli* LexA repressor protein, or the yeast GAL4 protein (Bartel et al., BioTechniques (1993) 14:920–924, Chasman et al., Mol. Cell. Biol. (1989) 9:4746–4749; Ma et al., Cell (1987) 48:847–853; Ptashne et al., Nature (1990) 346:329–331).

The prey fusion protein can be constructed using any suitable activation domain such as GAM4, VP-16, etc. The preys may contain useful moieties such as nuclear localization signals (Ylikomi et al., EMBO J. (1992) 11:3681–3694; Dingwall and Laskey, Trends Biochem. Sci. Trends Biochem. Sci. (1991) 16:479481) or epitope tags (Allen et al., Trends Biochem. Sci. Trends Biochem. Sci. (1995) 20:511–516) to facilitate isolation of the encoded proteins.

Any reporter gene can be used that has a detectable phenotype such as reporter genes that allow cells expressing them to be selected by growth on appropriate medium (e.g. HIS3, LEU2 described by Chien et al., PNAS (1991) 88:9572–9582; and Gyuris et al., Cell (1993) 75:791–803). Other reporter genes, such as LacZ and GFP, allow cells expressing them to be visually screened (Chien et al., supra).

Although the preferred host for two-hybrid screening is the yeast, the host cell in which the interaction assay and transcription of the reporter gene occurs can be any cell, such as mammalian (e.g. monkey, mouse, rat, human, bovine), chicken, bacterial, or insect cells. Various vectors and host strains for expression of the two fusion protein populations in yeast can be used (U.S. Pat. No. 5,468,614; Bartel et al., Cellular Interactions in Development (1993) Hartley, ed., Practical Approach Series xviii, IRL Press at Oxford University Press, New York, N.Y., pp. 153–179; and Fields and Sternglanz, Trends In Genetics (1994) 10:286–292). As an example of a mammalian system, interaction of activation tagged VP16 derivatives with a GAL4-derived bait drives expression of reporters that direct the synthesis of hygromycin B phosphotransferase, chloramphenicol acetyltransferase, or CD4 cell surface antigen (Fearon et al., PNAS (1992) 89:7958–7962). As another example, interaction of VP16-tagged derivatives with GAL4-derived baits drives the synthesis of SV40 T antigen, which in turn promotes the replication of the prey plasmid, which carries an SV40 origin (Vasavada et al., PNAS (1991) 88:10686–10690).

Typically, the bait dmVEGFR gene and the prey library of chimeric genes are combined by mating the two yeast strains on solid or liquid media for a period of approximately 6–8 hours. The resulting diploids contain both kinds of chimeric genes, i.e., the DNA-binding domain fusion and the activation domain fusion.

Transcription of the reporter gene can be detected by a linked replication assay in the case of SV40 T antigen (described by Vasavada et al., supra) or using immunoassay methods, preferably as described in Alam and Cook (Anal. Biochem. (1990)188:245–254). The activation of other reporter genes like URA3, HIS3, LYS2, or LEU2 enables the cells to grow in the absence of uracil, histidine, lysine, or leucine, respectively, and hence serves as a selectable marker. Other types of reporters are monitored by measuring a detectable signal. For example, GFP and lacZ have gene products that are fluorescent and chromogenic, respectively. After interacting proteins have been identified, the DNA sequences encoding the proteins can be isolated. In one method, the activation domain sequences or DNA-binding domain sequences (depending on the prey hybrid used) are amplified, for example, by PCR using pairs of oligonucleotide primers specific for the coding region of the DNA binding domain or activation domain. Other known amplification methods can be used, such as ligase chain reaction, use of Q replicase, or various other methods described (see Kricka et al., Molecular Probing, Blotting, and Sequencing (1995) Academic Press, New York, Chapter 1 and Table IX).

If a shuttle (yeast to *E. coli*) vector is used to express the fusion proteins, the DNA sequences encoding the proteins can be isolated by transformation of *E. coli* using the yeast DNA and recovering the plasmids from *E. coli*. Alternatively, the yeast vector can be isolated, and the insert encoding the fusion protein subcloned into a bacterial expression vector, for growth of the plasmid in *E. coli.*

A limitation of the two-hybrid system occurs when transmembrane portions of proteins in the bait or the prey fusions are used. This occurs because most two-hybrid systems are designed to function by formation of a functional transcription activator complex within the nucleus, and use of transmembrane portions of the protein can interfere with proper association, folding, and nuclear transport of bait or prey segments (Ausubel et al., supra; Allen et al., supra). Since the dmVEGFR protein is a transmembrane protein, it is preferred that intracellular or extracellular domains be used for bait in a two-hybrid scheme.

Antibodies to dmVEGFR and Immunoassays dmVEGFR proteins encoded by any of SEQ ID NOs:2, 4, 6, or 8 and derivatives and fragments thereof, such as those discussed above, may be used as an immunogen to generate monoclonal or polyclonal antibodies and antibody fragments or derivatives (e.g. chimeric, single chain, Fab fragments). For example, fragments of a dmVEGFR protein, preferably those identified as hydrophilic, are used as immunogens for antibody production using art-known methods such as by hybridomas; production of monoclonal antibodies in germ-free animals (PCT/US90/02545); the use of human hybridomas (Cole et al., PNAS (1983) 80:2026–2030; Cole et al., in Monoclonal Antibodies and Cancer Therapy (1985) Alan R. Liss, pp. 77–96), and production of humanized antibodies (Jones et al., Nature (1986) 321:522–525; U.S. Pat. No. 5,530,101). In a particular embodiment, dmVEGFR polypeptide fragments provide specific antigens and/or immunogens, especially when coupled to carrier proteins. For example, peptides are covalently coupled to keyhole limpet antigen (KLH) and the conjugate is emulsified in Freund's complete adjuvant. Laboratory rabbits are immunized according to conventional protocol and bled. The presence of specific antibodies is assayed by solid phase immunosorbent assays using immobilized corresponding polypeptide. Specific activity or function of the antibodies produced may be determined by convenient in vitro, cell-based, or in vivo assays: e.g. in vitro binding assays, etc. Binding affinity may be assayed by determination of equilibrium constants of antigen-antibody association (usually at least about $10^7$M-, preferably at least about $10^8$ $M^{-1}$, more preferably at least about $10^9$ $M^{-1}$).

Immunoassays can be used to identify proteins that interact with or bind to dmVEGFR protein. Various assays are available for testing the ability of a protein to bind to or compete with binding to a wild-type dmVEGFR protein or for binding to an anti-dmVEGFR protein antibody. Suitable assays include radioimmunoassays, ELISA (enzyme linked immunosorbent assay), immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, immunoelectrophoresis assays, etc.

Identification of Potential Drug and Pesticide Targets

VEGFR genes or interacting genes can be assessed as potential drug or pesticide targets. Putative drugs and molecules can be applied onto whole insects, nematodes, and other small invertebrate metazoans, and the ability of the compounds to modulate (e.g. block or enhance) dmVEGFR activity can be observed. Alternatively, the effect of various compounds on dmVEGFRs can be assayed using cells that have been engineered to express one or more dmVEGFRs and associated proteins.

Assays of Compounds on Worms

In a typical worm assay, the compounds to be tested are dissolved in DMSO or other organic solvent, mixed with a bacterial suspension at various test concentrations, preferably OP50 strain of bacteria (Brenner, Genetics (1974) 110:421–440), and supplied as food to the a worms. The population of worms to be treated can be synchronized larvae (Sulston and Hodgkin, in The nematode C. elegans (1988), supra) or adults or a mixed-stage population of animals.

Adult and larval worms are treated with different concentrations of compounds, typically ranging from 1 mg/ml to 0.001 mg/ml. Behavioral aberrations, such as a decrease in motility and growth, and morphological aberrations, sterility, and death are examined in both acutely and chronically treated adult and larval worms. For the acute assay, larval and adult worms are examined immediately after application of the compound and re-examined periodically (every 30 minutes) for 5–6 hours. Chronic or long-term assays are performed on worms and the behavior of the treated worms is examined every 8–12 hours for 4–5 days. In some circumstances, it is necessary to reapply the pesticide to the treated worms every 24 hours for maximal effect.

Assays of Compounds on Insects

Potential insecticidal compounds can be administered to insects in a variety of ways, including orally (including addition to synthetic diet, application to plants or prey to be consumed by the test organism), topically (including spraying, direct application of compound to animal, allowing animal to contact a treated surface), or by injection. Insecticides are typically very hydrophobic molecules and must commonly be dissolved in organic solvents, which are allowed to evaporate in the case of methanol or acetone, or at low concentrations can be included to facilitate uptake (ethanol, dimethyl sulfoxide).

The first step in an insect assay is usually the determination of the minimal lethal dose (MLD) on the insects after a chronic exposure to the compounds. The compounds are usually diluted in DMSO, and applied to the food surface bearing 0–48 hour old embryos and larvae. In addition to MLD, this step allows the determination of the fraction of eggs that hatch, behavior of the larvae, such as how they move/feed compared to untreated larvae, the fraction that survive to pupate, and the fraction that eclose (emergence of the adult insect from puparium). Based on these results more detailed assays with shorter exposure times may be designed, and larvae might be dissected to look for obvious morphological defects. Once the MLD is determined, more specific acute and chronic assays can be designed.

In a typical acute assay, compounds are applied to the food surface for embryos, larvae, or adults, and the animals are observed after 2 hours and after an overnight incubation. For application on embryos, defects in development and the percent that survive to adulthood are determined. For larvae, defects in behavior, locomotion, and molting may be observed. For application on adults, behavior and neurological defects are observed, and effects on fertility are noted.

For a chronic exposure assay, adults are placed on vials containing the compounds for 48 hours, then transferred to a clean container and observed for fertility, neurological defects, and death.

Assay of Compounds on Cell Cultures

Compounds that modulate (e.g. block or enhance) dmVEGFR activity may also be assayed using cell culture. For example, the effect of exogenously added compounds cells expressing dmVEGFR may be screened for their ability to modulate the activity of dmVEGFR genes based upon measurements of cell proliferation. Assays for changes in kinase activity can be performed on cultured cells expressing endogenous normal or mutant dmVEGFRs. Such studies also can be performed on cells transfected with vectors capable of expressing the dmVEGFRs, or functional domains of one of the dmVEGFRs, in normal or mutant form. In addition, to enhance the signal measured in such assays, cells may be cotransfected with genes encoding dmVEGFR proteins.

For example, binding assays with the soluble dmVEGFRs generated from cells expressing the receptors can be performed essentially as described by Piossek et al., J. Biol. Chem. (1999) 274:5612–5619. Once it has been determined that a compound is able to bind to the receptor, it can then be tested for its ability to induce endothelial cell proliferation using methods described by Cao et al. (PNAS (1998) 95:14389–14394). Briefly, endothelial cells expressing dmVEGFR are seeded in single wells of multi-well culture plate, compounds of various concentrations are added in triplicate to the wells containing the cells. Cells are then counted to check for proliferation.

Identification of small molecules and compounds as potential pharmaceutical compounds from large chemical libraries requires high-throughput screening (HTS) methods (Bolger, Drug Discovery Today (1999) 4:251–253). Several of the assays mentioned herein can lend themselves to such screening methods. For example, cells or cell lines expressing wild type or mutant dmVEGFR protein or its fragments, and a reporter gene can be subjected to compounds of interest, and depending on the reporter genes, interactions can be measured using a variety of methods such as color detection, fluorescence detection (e.g. GFP), autoradiography, scintillation analysis, etc. Compounds that selectively modulate dmVEGFR activity are identified as potential drug candidates having dmVEGFR specificity.

Generation and Genetic Analysis of Animals and Cell Lines with Altered Expression of VEGFR Gene Both genetically modified animal models (i.e. in vivo models), such as *C. elegans* and Drosophila, and in vitro models such as genetically engineered cell lines expressing or mis-expressing dmVEGFR pathway genes, are useful for the functional analysis of these proteins. Model systems that display detectable phenotypes, can be used for the identification and characterization of dmVEGFR pathway genes or other genes of interest and/or phenotypes associated with the mutation or mis-expression of dmVEGFR pathway proteins. The term "mis-expression" as used herein encompasses mis-expression due to gene mutations. Thus, a mis-expressed dmVEGFR pathway protein may be one having an amino acid sequence that differs from wild-type (i.e. it is a derivative of the normal protein). A mis-expressed dmVEGFR pathway protein may also be one in which one or more amino acids have been deleted, and thus is a "fragment" of the normal protein. As used herein, "mis-expression" also includes ectopic expression (e.g. by altering the normal spatial or temporal expression), over-expression (e.g. by multiple gene copies), underexpression, non-expression (e.g. by gene knockout or blocking expression that would otherwise normally occur), and further, expression in ectopic tissues. As used in the following discussion concerning in vivo and in vitro models, the term "gene of interest" refers to a dmVEGFR pathway gene, or any other gene involved in regulation or modulation, or downstream effector of the dmVEGFR pathway.

The in vivo and in vitro models may be genetically engineered or modified so that they 1) have deletions and/or insertions of one or more dmVEGFR pathway genes, 2) harbor interfering RNA sequences derived from dmVEGFR pathway genes, 3) have had one or more endogenous dmVEGFR pathway genes mutated (e.g. contain deletions, insertions, rearrangements, or point mutations in dmVEGFR gene or other genes in the pathway), and/or 4) contain transgenes for mis-expression of wild-type or mutant forms of such genes. Such genetically modified in vivo and in vitro models are useful for identification of genes and proteins that are involved in the synthesis, activation, control, etc. of dmVEGFR pathway gene and/or gene products, and also downstream effectors of dmVEGFR function, genes regulated by dmVEGFR, etc. The model systems can also be used for testing potential pharmaceutical compounds that interact with the dmVEGFR pathway, for example by administering the compound to the model system using any suitable method (e.g. direct contact, ingestion, injection, etc.) and observing any changes in phenotype, for example defective movement, lethality, etc. Various genetic engineering and expression modification methods which can be used are well-known in the art, including chemical mutagenesis, transposon mutagenesis, antisense RNAi, dsRNAi, and transgene-mediated mis-expression.

Generating Loss-of-function Mutations by Mutagenesis

Loss-of-function mutations in an invertebrate metazoan dmVEGFR gene can be generated by any of several mutagenesis methods known in the art (Ashburner, In Drosophila melanogaster: A Laboratory Manual (1989), Cold Spring Harbor, N.Y., Cold Spring Harbor Laboratory Press: pp. 299–418; Fly pushing: The Theory and Practice of Drosophila melanogaster Genetics (1997) Cold Spring Harbor Press, Plainview, N.Y.; The nematode *C. elegans* (1988) Wood, Ed., Cold Spring Harbor Laboratory Press, Cold Spring harbor, N.Y.). Techniques for producing mutations in a gene or genome include use of radiation (e.g., X-ray, UV, or gamma ray); chemicals (e.g., EMS, MMS, ENU, formaldehyde, etc.); and insertional mutagenesis by mobile elements including dysgenesis induced by transposon insertions, or transposon-mediated deletions, for example, male recombination, as described below. Other methods of altering expression of genes include use of transposons (e.g., P element, EP-type "overexpression trap" element, mariner element, piggybac transposon, hermes, minos, sleeping beauty, etc.) to misexpress genes; gene targeting by homologous recombination; antisense; double-stranded RNA interference; peptide and RNA aptamers; directed deletions; homologous recombination; dominant negative alleles; and intrabodies.

Transposon insertions lying adjacent to a gene of interest can be used to generate deletions of flanking genomic DNA, which if induced in the germline, are stably propagated in subsequent generations. The utility of this technique in generating deletions has been-demonstrated and is well-known in the art. One version of the technique using collections of P element transposon induced recessive lethal mutations (P lethals) is particularly suitable for rapid identification of novel, essential genes in Drosophila (Cooley et al., Science (1988) 239:1121–1128; Spralding et al., PNAS (1995) 92:0824–10830). Since the sequence of the P elements are known, the genomic sequence flanking each transposon insert is determined either by plasmid rescue (Hamilton et al., PNAS (1991) 88:2731–2735) or by inverse polymerase chain reaction. A more recent version of the transposon insertion technique in male Drosophila using P elements is known as P-mediated male recombination (Preston and Engels, Genetics (1996) 144:1611–1638).

Gene targeting approaches using homologous recombination have proven to be successful in Drosophila (Rong and Golic, Science (2000) 288:2013–20018) and potentially provide a general method of generating directed mutations in any gene-of-interest. This method uses broken-ended extrachromosomal DNA, created in vivo, to produce homology-directed changes in a target locus. First, a "targeting construct" is designed for the gene-of-interest which allows the replacement of the normal endogenous gene with a specifically designed mutation, such as a deletion, insertion or point mutation, via homologous recombination. The targeting construct is typically carried in an appropriate transposon-mediated transgenesis vector (e.g. P element-, piggyBac-, hermes-, minos-, or mariner-based vectors) which inserts the targeting construct randomly within the genome of the organism. The targeting construct is converted to a recombinogenic extrachromosomal form by inducing the expression of separate transgenes encoding a site-specific recombinase (e.g. FLP, cre, Kw, etc.) which excises the targeting construct, and a rare-cutting site-specific endonuclease (e.g. SceI, CreI, HO, etc.) which generates recombinogenic ends that direct homologous recombination and gene replacement of the endogenous locus. Though this method has only been shown to work in Dros, it has application to worms, other animals, plants, algae etc.

Generating Loss-of-function Phenotypes Using RNA-based Methods dmVEGFR genes may be identified and/or characterized by generating loss-of-function phenotypes in animals of interest through RNA-based methods, such as antisense RNA (Schubiger and Edgar, Methods in Cell Biology (1994) 44:697–713). One form of the antisense RNA method involves the injection of embryos with an antisense RNA that is partially homologous to the gene of interest (in this case the dmVEGFR gene). Another form of the antisense RNA method involves expression of an antisense RNA partially homologous to the gene of interest by operably joining a portion of the gene of interest in the antisense orientation to a powerful promoter that can drive the expression of large quantities of antisense RNA, either generally throughout the animal or in specific tissues. Antisense RNA-generated loss-of-function phenotypes have been reported previously for several Drosophila genes including cactus, pecanex, and Krippel (LaBonne et al., Dev. Biol. (1989) 136(1): 1–16; Schuh and Jackle, Genome (1989) 31(1):422–425; Geisler et al., Cell (1992) 71(4):613–621).

Loss-of-function phenotypes can also be generated by cosuppression methods (Bingham Cell (1997) 90(3):385–387; Smyth, Curr. Biol. (1997) 7(12):793–795; Que and Jorgens Genet. (1998) 22(1):100–109). Cosuppression is a phenomenon of reduced gene expression produced by expression or injection of a sense strand RNA corresponding to a partial segment of the gene of interest. Cosuppression effects have been employed extensively in plants and *C. elegans* to generate loss-of-function phenotypes, and there is a single report of cosuppression in Drosophila, where reduced expression of the Adh gene was induced from a white-Adh transgene using cosuppression methods (Pal-Bhadra et al., Cell (1997) 90(3):479–490).

Another method for generating loss-of-function phenotypes is by double-stranded RNA interference (dsRNAi). This method is based on the interfering properties of double-stranded RNA derived from the coding regions of gene, and has proven to be of great utility in genetic studies of *C. elegans* (Fire et al., Nature (1998) 391:806–811), and can also be used to generate loss-of-function phenotypes in Drosophila (Kennerdell and Carthew, Cell (1998) 95:1017–1026; Misquitta and Patterson PNAS (1999) 96:1451–1456). In one example of this method, complementary sense and antisense RNAs derived from a substantial portion of a gene of interest, such as dmVEGFR gene, are synthesized in vitro. The resulting sense and antisense RNAs are annealed in an injection buffer, and the double-stranded RNA injected or otherwise introduced into animals (such as in their food or by soaking in the buffer containing the RNA). Progeny of the injected animals are then inspected for phenotypes of interest (PCT publication no. WO99/32619).

Generating Loss-of-function Phenotypes Using Peptide and RNA Aptamers

Another method for generating loss-of-function phenotypes is by the use of peptide aptamers, which are peptides or small polypeptides that act as dominant inhibitors of protein function. Peptide aptamers specifically bind to target proteins, blocking their function ability (Kolonin and Finley, PNAS (1998) 95:14266–14271). Due to the highly selective nature of peptide aptamers, they may be used not only to target a specific protein, but also to target specific functions of a given protein (e.g. kinase function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein may be isolated by a variety of techniques known in the art. In one method, they are isolated from random peptide libraries by yeast two-hybrid screens (Xu et al., PNAS (1997) 94:12473–12478). They can also be isolated from phage libraries (Hoogenboom et al., Immunotechnology (1998) 4:1–20) or chemically generated peptides/libraries.

RNA aptamers are specific RNA ligands for proteins, that can specifically inhibit protein function of the gene (Good et al., Gene Therapy (1997) 4:45–54; Ellington. et al., Biotechnol. Annu. Rev. (1995) 1:185–214). In vitro selection methods can be used to identify RNA aptamers having a selected specificity (Bell et al., J. Biol. Chem. (1998) 273:14309–14314). It has been demonstrated that RNA aptamers can inhibit protein function in Drosophila (Shi et al., Proc. Natl. Acad. Sci USA (19999) 96:10033–10038). Accordingly, RNA aptamers can be used to decrease the expression of dmVEGFR protein or derivative thereof, or a protein that interacts with the dmVEGFR protein.

Transgenic animals can be generated to test peptide or RNA aptamers in vivo (Kolonin, MG, and Finley, RL, Genetics, 1998 95:4266–4271). For example, transgenic Drosophila lines expressing the desired aptamers may be generated by P element mediated transformation (discussed below). The phenotypes of the progeny expressing the aptamers can then be characterized.

Generating Loss of Function Phenotypes Using Intrabodies

Intracellularly expressed antibodies, or intrabodies, are single-chain antibody molecules designed to specifically bind and inactivate target molecules inside cells. Intrabodies have been used in cell assays and in whole organisms such as Drosophila (Chen et al., Hum. Gen. Ther. (1994) 5:595–601; Hassanzadeh et al., Febs Lett. (1998) 16(1, 2):75–80 and 81–86). expression vectors can be constructed with intrabodies that react specifically with dmVEGFR protein. These vectors can be introduced into model organisms and studied in the same manner as described above for aptamers.

Transgenesis

Typically, transgenic animals are created that contain gene fusions of the coding regions of the dmVEGFR gene (from either genomic DNA or cDNA) or genes engineered to encode antisense RNAs, cosuppression RNAs, interfering dsRNA, RNA aptamers, peptide aptamers, or intrabodies operably joined to a specific promoter and transcriptional enhancer whose regulation has been well characterized, preferably heterologous promoters/enhancers (i.e. promoters/enhancers that are non-native to the dmVEGFR pathway genes being expressed).

Methods are well known for incorporating exogenous nucleic acid sequences into the genome of animals or cultured cells to create transgenic animals or recombinant cell lines. For invertebrate animal models, the most common methods involve the use of transposable elements. There are several suitable transposable elements that can be used to incorporate nucleic acid sequences into the genome of model organisms. Transposable elements are particularly useful for inserting sequences into a gene of interest so that the encoded protein is not properly expressed, creating a “knock-out” animal having a loss-of-function phenotype. Techniques are well-established for the use of P element in Drosophila (Rubin and Spradling, Science (1982) 218:348–53; U.S. Pat. No. 4,670,388) and Tc1 in *C. elegans* (Zwaal et al., Proc. Natl. Acad. Sci. U.S.A. (1993) 90:7431–7435*; and Caenorhabditis elegans*: Modem Biological Analysis of an Organism (1995) Epstein and Shakes, Eds.). Other Tc1-like transposable elements can be used such as minos, mariner and sleeping beauty. Additionally, transposable elements that function in a variety of species, have been identified, such as PiggyBac (Thibault et al., Insect Mol Biol (1999) 8(1): 119–23), hobo, and hermes.

P elements, marked P elements, or piggybac elements are preferred for the isolation of loss-of-function mutations in Drosophila dmVEGFR genes because of the precise molecular mapping of these genes, depending on the availability and proximity of preexisting insertions for use as a localized transposon source (Hamilton and Zinn, Methods in Cell Biology (1994) 44:81–94; and Wolfner and Goldberg, Methods in Cell Biology (1994) 44:33–80). Typically, transposable elements are used which contain one or more elements that allow detection of animals containing the transposable element. Most often, marker genes are used that affect the eye color of Drosophila, such as derivatives of the Drosophila white or rosy genes (Rubin and Spradling, Science (1982) 218(4570):348–353; and Klemenz et al., Nucleic Acids Res. (1987) 15(10):3947–3959). However, in principle, any gene can be used as a marker that causes a reliable and easily scored phenotypic change in transgenic animals. Various other markers include bacterial plasmid sequences having selectable markers such as ampicillin resistance (Steller and Pirrotta, EMBO. J. (1985) 4:167–171); and lacZ sequences fused to a weak general promoter to detect the presence of enhancers with a developmental expression pattern of interest (Bellen et al., Genes Dev. (1989) 3(9):1288–1300).

A preferred method of transposon mutagenesis in Drosophila employs the “local hopping” method described by Tower et al. (Genetics (1993) 133:347–359). Each new P insertion line can be tested molecularly for transposition of the P element into the gene of interest (e.g. dmVEGFR) by assays based on PCR. For each reaction, one PCR primer is used that is homologous to sequences contained within the P element and a second primer is homologous to the coding region or flanking regions of the gene of interest. Products of the PCR reactions are detected by agarose gel electrophoresis. The sizes of the resulting DNA fragments reveal the site of P element insertion relative to the gene of interest. Alternatively, Southern blotting and restriction mapping using DNA probes derived from genomic DNA or cDNAs of the gene of interest can be used to detect transposition events that rearrange the genomic DNA of the gene. P transposition events that map to the gene of interest can be assessed for phenotypic effects in heterozygous or homozygous mutant Drosophila.

In another embodiment, Drosophila lines carrying P insertions in the gene of interest, can be used to generate localized deletions using known methods (Kaiser, Bioassays (1990) 12(6):297–301; Harnessing the power of Drosophila genetics, In Drosophila melanogaster: Practical Uses in Cell and Molecular Biology, Goldstein and Fyrberg, Eds., Academic Press, Inc. San Diego, Calif.). This is particularly useful if no P element transpositions are found that disrupt the gene of interest. Briefly, flies containing P elements inserted near the gene of interest are exposed to a further round of transposase to induce excision of the element. Progeny in which the transposon has excised are typically identified by loss of the eye color marker associated with the transposable element. The resulting progeny will include flies with either precise or imprecise excision of the P element, where the imprecise excision events often result in deletion of genomic DNA neighboring the site of P insertion. Such progeny are screened by molecular techniques to identify deletion events that remove genomic sequence from the gene of interest, and assessed for phenotypic effects in heterozygous and homozygous mutant Drosophila.

In *C. elegans*, Tc1 transposable element can be used for directed mutagenesis of a gene of interest. Typically, a Tc1 library is prepared by the methods of Zwaal et al., supra and Plasterk, supra, using a strain in which the Tc1 transposable element is highly mobile and present in a high copy number. The library is screened for Tc1 insertions in the region of interest using PCR with one set of primers specific for Tc1 sequence and one set of gene-specific primers and *C. elegans* strains that contain Tc1 transposon insertions within the gene of interest are isolated.

In addition to creating loss-of-function phenotypes, transposable elements can be used to incorporate the gene of interest, or mutant or derivative thereof, as an additional gene into any region of an animal's genome resulting in mis-expression (including over-expression) of the gene. A preferred vector designed specifically for misexpression of genes in transgenic Drosophila, is derived from pGMR (Hay et al., Development (1994) 120:2121–2129), is 9Kb long, and contains: an origin of replication for *E. coli*; an ampicillin resistance gene; P element transposon 3' and 5' ends to mobilize the inserted sequences; a White marker gene; an expression unit comprising the TATA region of hsp70 enhancer and the 3' untranslated region of xtubulin gene. The expression unit contains a first multiple cloning site (MCS) designed for insertion of an enhancer and a second MCS located 500 bases downstream, designed for the insertion of a gene of interest. As an alternative to transposable elements, homologous recombination or gene targeting techniques can be used to substitute a gene of interest for one or both copies of the animal's homologous gene. The transgene can be under the regulation of either an exogenous or an endogenous promoter element, and be inserted as either a minigene or a large genomic fragment. In one application, gene function can be analyzed by ectopic expression, using, for example, Drosophila (Brand et al., Methods in Cell Biology (1994) 44:635–654) or *C. elegans* (Mello and Fire, Methods in Cell Biology (1995) 48:451–482).

Examples of well-characterized heterologous promoters that may be used to create the transgenic animals include heat shock promoters/enhancers, which are useful for temperature induced mis-expression. In Drosophila, these include the hsp70 and hsp83 genes, and in *C. elegans*, include hsp 16–2 and hsp 16–41. Tissue specific promoters/enhancers are also useful, and in Drosophila, include eyeless (Mozer and Benzer, Development (1994) 120:1049–1058), sevenless (Bowtell et al., PNAS (1991) 88(15):6853–6857), and glass-responsive promoters/enhancers (Quiring et al., Science (1994) 265:785–789) which are useful for expression in the eye; and enhancers/promoters derived from the dpp or vestigal genes which are useful for expression in the wing (Staehling-Hampton et al., Cell Growth Differ. (1994) 5(6):585–593; Kim et al., Nature (1996) 382:133–138). Finally, where it is necessary to restrict the activity of dominant active or dominant negative transgenes to regions where the pathway is normally active, it may be useful to use endogenous promoters of genes in the pathway, such as the dmVEGFR pathway genes.

In *C. elegans*, examples of useful tissue specific promoters/enhancers include the myo-2 gene promoter, useful for pharyngeal muscle-specific expression; the hlh-1 gene promoter, useful for body-muscle-specific expression; and the gene promoter, useful for touch-neuron-specific gene expression. In a preferred embodiment, gene fusions for directing the mis-expression of dmVEGFR pathway genes are incorporated into a transformation vector which is injected into nematodes along with a plasmid containing a dominant selectable marker, such as rol-6. Transgenic animals are identified as those exhibiting a roller phenotype, and the transgenic animals are inspected for additional phenotypes of interest created by mis-expression of the dmVEGFR pathway gene.

In Drosophila, binary control systems that employ exogenous DNA are useful when testing the mis-expression of genes in a wide variety of developmental stage-specific and tissue-specific patterns. Two examples of binary exogenous regulatory systems include the UAS/GALA system from yeast (Hay et al., PNAS (1997) 94(10):5195–5200; Ellis et al., Development (1993) 119(3):855–865), and the "Tet system" derived from *E. coli* (Bello et al., Development (1998) 125:2193–2202). The UAS/GALM system is a well-established and powerful method of mis-expression in Drosophila which employs the UASG upstream regulatory sequence for control of promoters by the yeast GAL4 transcriptional activator protein (Brand and Perrimon, Development (1993) 118(2):401–15). In this approach, transgenic Drosophila, termed "target" lines, are generated where the gene of interest to be mis-expressed is operably fused to an appropriate promoter controlled by UASG. Other transgenic Drosophila strains, termed "driver" lines, are generated where the GAL4 coding region is operably fused to promoters/enhancers that direct the expression of the GALA activator protein in specific tissues, such as the eye, wing, nervous system, gut, or musculature. The gene of interest is not expressed in the target lines for lack of a transcriptional activator to drive transcription from the promoter joined to the gene of interest. However, when the UAS-target line is crossed with a GAL4 driver line, mis-expression of the gene of interest is induced in resulting progeny in a specific pattern that is characteristic for that GAL4 line. The technical simplicity of this approach makes it possible to sample the effects of directed mis-expression of the gene of interest in a wide variety of tissues by generating one transgenic target line with the gene of interest, and crossing that target line with a panel of pre-existing driver lines.

In the "Tet" binary control system, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. The driver lines are crossed with transgenic Drosophila target lines where the coding region for the gene of interest to be mis-expressed is operably fused to a promoter that possesses a tTA-responsive regulatory element. When the resulting progeny are supplied with food supplemented with a sufficient amount of tetracycline, expression of the gene of interest is blocked. Expression of the gene of interest can be induced at will simply by removal of tetracycline from the food. Also, the level of expression of the gene of interest can be adjusted by varying the level of tetracycline in the food. Thus, the use of the Tet system as a binary control mechanism for mis-expression has the advantage of providing a means to control the amplitude and timing of mis-expression of the gene of interest, in addition to spatial control. Consequently, if a gene of interest (e.g. a dmVEGFR gene) has lethal or deleterious effects when mis-expressed at an early stage in development, such as the embryonic or larval stages, the function of the gene of interest in the adult can still be assessed by adding tetracycline to the food during early stages of development and removing tetracycline later so as to induce mis-expression only at the adult stage.

Dominant negative mutations, by which the mutation causes a protein to interfere with the normal function of a wild-type copy of the protein, and which can result in loss-of-function or reduced-function phenotypes in the presence of a normal copy of the gene, can be made using known methods (Hershkowitz, Nature (1987) 329:219–222). In the case of active monomeric proteins, overexpression of an inactive form, achieved, for example, by linking the mutant gene to a highly active promoter, can cause competition for natural. substrates or ligands sufficient to significantly reduce net activity of the normal protein. Alternatively, changes to active site residues can be made to create a virtually irreversible association with a target. The extracellular domain of VEGFR may be used as a dominant negative form to inhibit activity of VEGFR. SEQ ID NOs:7 and 8 are an isolated mutant cDNA and its protein translation, respectively, representing only the extracellular portion of dmVEGFR.

Assays for Change in Gene Expression

Various expression analysis techniques may be used to identify genes which are differentially expressed between a cell line or an animal expressing a wild type dmVEGFR gene compared to another cell line or animal expressing a mutant dmVEGFR gene. Such expression profiling techniques include differential display, serial analysis of gene expression (SAGE), transcript profiling coupled to a gene database query, nucleic acid array technology, subtractive hybridization, and proteome analysis (e.g. mass-spectrometry and two-dimensional protein gels). Nucleic acid array technology may be used to determine a global (i.e., genome-wide) gene expression pattern in a normal animal for comparison with an animal having a mutation in dmVEGFR gene. Gene expression profiling can also be used to identify other genes (or proteins) that may have a functional relation to dmVEGFR (e.g. may participate in a signaling pathway with the dmVEGFR gene). The genes are identified by detecting changes in their expression levels following mutation, i.e., insertion, deletion or substitution in, or over-expression, under-expression, mis-expression or knock-out, of the dmVEGFR gene.

Phenotypes Associated with VEGFR Pathway Gene Mutations

After isolation of model animals carrying mutated or mis-expressed dmVEGFR pathway genes or inhibitory RNAs, animals are carefully examined for phenotypes of interest. For analysis of dmVEGFR pathway genes that have been mutated (i.e. deletions, insertions, and/or point mutations) animal models that are both homozygous and heterozygous for the altered dmVEGFR pathway gene are analyzed. Examples of specific phenotypes that may be investigated include lethality; sterility; feeding behavior, perturbations in neuromuscular function including alterations in motility, and alterations in sensitivity to pharmaceuticals and other compounds. Some phenotypes more specific to flies include alterations in: adult behavior such as, flight ability, walking, grooming, phototaxis, mating or egg-laying; alterations in the responses of sensory organs, changes in the morphology, size or number of adult tissues such as, eyes, wings, legs, bristles, antennae, gut, fat body, gonads, trachea, and musculature; larval tissues such as mouth parts, cuticles, internal tissues or imaginal discs; alterations in production of organs and tissues such as hemopoeisis, or larval behavior such as feeding, molting, crawling, or puparian formation; or developmental defects in any germline or embryonic tissues. Some phenotypes more specific to nematodes include: locomotory, egg laying, chemosensation, male mating, and intestinal expulsion defects. In various cases, single phenotypes or a combination of specific phenotypes in model organisms might point to specific genes or a specific pathway of genes, which facilitate the cloning process.

Genomic sequences containing a dmVEGFR pathway gene can be used to confirm whether an existing mutant insect or worm line corresponds to a mutation in one or more dmVEGFR pathway genes, by rescuing the mutant phenotype. Briefly, a genomic fragment containing the dmVEGFR pathway gene of interest and potential flanking regulatory regions can be subcloned into any appropriate insect (such a's Drosophila) or worm (such as *C. elegans*) transformation vector, and injected into the animals. For Drosophila, an appropriate helper plasmid is used in the injections to supply transposase for transposon-based vectors. Resulting germ-line transformants are crossed for complementation testing to an existing or newly created panel of Drosophila or *C. elegans* lines whose mutations have been mapped to the vicinity of the gene of interest (Fly Pushing: The Theory and Practice of Drosophila Genetics, supra; and Caenorhabditis elegans: Modern Biological Analysis of an Organism (1995), Epstein and Shakes, eds.). If a mutant line is discovered to be rescued by this genomic fragment, as judged by complementation of the mutant phenotype, then the mutant line likely harbors a mutation in the dmVEGFR pathway gene. This prediction can be further confirmed by sequencing the dmVEGFR pathway gene from the mutant line to identify the lesion in the dmVEGFR pathway gene.

Identification of Genes That Modify VEGFR Genes

The characterization of new phenotypes created by mutations or misexpression in dmVEGFR genes enables one to test for genetic interactions between dmVEGFR genes and other genes that may participate in the same, related, or interacting genetic or biochemical pathway(s). Individual genes can be used as starting points in large-scale genetic modifier screens as described in more detail below. Alternatively, RNAi methods can be used to simulate loss-of-function mutations in the genes being analyzed. It is of particular interest to investigate whether there are any interactions of dmVEGFR genes with other well-characterized genes, particularly genes involved in endothelial cell signaling with kinase activity.

Genetic Modifier Screens

A genetic modifier screen using invertebrate model organisms is a particularly preferred method for identifying genes that interact with dmVEGFR genes, because large numbers of animals can be systematically screened making it more possible that interacting genes will be identified. In Drosophila, a screen of up to about 10,000 animals is considered to be a pilot-scale screen. Moderate-scale screens usually employ about 10,000 to about 50,000 flies, and large-scale screens employ greater than about 50,000 flies. In a genetic modifier screen, animals having a mutant phenotype due to a mutation in or misexpression of one or more dmVEGFR genes are further mutagenized, for example by chemical mutagenesis or transposon mutagenesis.

The procedures involved in typical Drosophila genetic modifier screens are well-known in the art (Wolfner and Goldberg, Methods in Cell Biology (1994) 44:33–80; and Karim et al., Genetics (1996) 143:315–329). The procedures used differ depending upon the precise nature of the mutant allele being modified. If the mutant allele is genetically recessive, as is commonly the situation for a loss-of-function allele, then most typically males, or in some cases females, which carry one copy of the mutant allele are exposed to an effective mutagen, such as EMS, MMS, ENU, triethylamine, diepoxyalkanes, ICR-170, formaldehyde, X-rays, gamma rays, or ultraviolet radiation. The mutagenized animals are crossed to animals of the opposite sex that also carry the mutant allele to be modified. In the case where the mutant allele being modified is genetically dominant, as is commonly the situation for ectopically expressed genes, wild type males are mutagenized and crossed to females carrying the mutant allele to be modified.

The progeny of the mutagenized and crossed flies that exhibit either enhancement or suppression of the original phenotype are presumed to have mutations in other genes, called "modifier genes", that participate in the same phenotype-generating pathway. These progeny are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis.

Standard techniques used for the mapping of modifiers that come from a genetic screen in Drosophila include meiotic mapping with visible or molecular genetic markers; male-specific recombination mapping relative to P-element insertions; complementation analysis with deficiencies, duplications, and lethal P-element insertions; and cytological analysis of chromosomal aberrations (Fly Pushing: Theory and Practice of Drosophila Genetics, supra; *Drosophila: A Laboratory Handbook*, supra). Genes corresponding to modifier mutations that fail to complement a lethal P-element may be cloned by plasmid rescue of the genomic sequence surrounding that P-element. Alternatively, modifier genes may be mapped by phenotype rescue and positional cloning (Sambrook et al., supra).

Newly identified modifier mutations can be tested directly for interaction with other genes of interest known to be involved or implicated with dmVEGFR genes using methods described above. Also, the new modifier mutations can be tested for interactions with genes in other pathways that are not believed to be related to receptor tyrosine kinase signaling (e.g. nanos in Drosophila). New modifier mutations that exhibit specific genetic interactions with other genes implicated in neuronal signaling, but not interactions with genes in unrelated pathways, are of particular interest.

The modifier mutations may also be used to identify "complementation groups". Two modifier mutations are considered to fall within the same complementation group if animals carrying both mutations in trans exhibit essentially the same phenotype as animals that are homozygous for each mutation individually and, generally are lethal when in trans to each other (Fly Pushing: The Theory and Practice of Drosophila Genetics, supra). Generally, individual complementation groups defined in this way correspond to individual genes.

When dmVEGFR modifier genes are identified, homologous genes in other species can be isolated using procedures based on cross-hybridization with modifier gene DNA probes, PCR-based strategies with primer sequences derived from the modifier genes, and/or computer searches of sequence databases. For therapeutic applications related to the function of dmVEGFR genes, human and rodent homologues of the modifier genes are of particular interest.

Although the above-described Drosophila genetic modifier screens are quite powerful and sensitive, some genes that interact with dmVEGFR genes may be missed in this approach, particularly if there is functional redundancy of those genes. This is because the vast majority of the mutations generated in the standard mutagenesis methods will be loss-of-function mutations, whereas gain-of-function mutations that could reveal genes with functional redundancy will be relatively rare. Another method of genetic screening in Drosophila has been developed that focuses specifically on systematic gain-of-function genetic screens (Rorth et al., Development (1998) 125:1049–1057). This method is based on a modular mis-expression system utilizing components of the GAL4JUAS system (described above) where a modified P element, termed an "enhanced P" (EP) element, is genetically engineered to contain a GAM4-responsive UAS element and promoter. Any other transposons can also be used for this system. The resulting transposon is used to randomly tag genes by insertional mutagenesis (similar to the method of P element mutagenesis described above). Thousands of transgenic Drosophila strains, termed EP lines, can be generated, each containing a specific UAS-tagged gene. This approach takes advantage of the preference of P elements to insert at the 5'-ends of genes. Consequently, many of the genes that are tagged by insertion of EP elements become operably fused to a GAL4-regulated promoter, and increased expression or mis-expression of the randomly tagged gene can be induced by crossing in a GAL4 driver gene.

Systematic gain-of-function genetic screens for modifiers of phenotypes induced by mutation or mis-expression of a dmVEGFR gene can be performed by crossing several thousand Drosophila EP lines individually into a genetic background containing a mutant or mis-expressed dmVEGFR gene, and further containing an appropriate GALA driver transgene. It is also possible to remobilize the EP elements to obtain novel insertions. The progeny of these crosses are then analyzed for enhancement or suppression of the original mutant phenotype as described above. Those identified as having mutations that interact with the dmVEGFR gene can be tested further to verify the reproducibility and specificity of this genetic interaction. EP insertions that demonstrate a specific genetic interaction with a mutant or mis-expressed dmVEGFR gene, have a physically tagged dmVEGFR which can be identified and sequenced using PCR or hybridization screening methods, allowing the isolation of the genomic DNA adjacent to the position of the EP element insertion.

EXAMPLES

The following examples describe the isolation and assembly of the nucleic acid sequence of SEQ ID NOs:1, 3, 5, and 7, and how these sequences, and derivatives and fragments thereof, as well as other dmVEGFR pathway nucleic acids and gene products can be used for genetic studies to elucidate mechanisms of the dmVEGFR pathway as well as the discovery of potential pharmaceutical agents that interact with the pathway.

These Examples are provided merely as illustrative of various aspects of the invention and should not be construed to limit the invention in any way.

Example 1

Preparation of Drosophila cDNA Library

A Drosophila expressed sequence tag (EST) cDNA library was prepared as follows. Tissue from mixed stage embryos (0–20 hour), imaginal disks and adult fly heads were collected and total RNA was prepared. Mitochondrial rRNA was removed from the total RNA by hybridization with biotinylated rRNA specific oligonucleotides and the resulting RNA was selected for p6lyadenylated rnRNA. The resulting material was then used to construct a random primed library. First strand cDNA synthesis was primed using a six nucleotide random primer. The first strand cDNA was then tailed with terminal transferase to add approximately 15 dGTP molecules. The second strand was primed using a primer which contained a Not1 site followed by a 13 nucleotide C-tail to hybridize to the G-tailed first strand cDNA. The double stranded cDNA was ligated with BstX1 adaptors and digested with Not1. The cDNA was then fractionated by size by electrophoresis on an agarose gel and the cDNA greater than 700 bp was purified. The cDNA was ligated with Not1, BstX1 digested pCDNA–sk+vector (a derivative of pBluescript, Stratagene) and used to transform *E. coli* (XL1blue). The final complexity of the library was $6\times10^6$ independent clones.

The cDNA library was normalized using a modification of the method described by Bonaldo et al. (Genome Research (1996) 6:791–806). Biotinylated driver was prepared from the cDNA by PCR amplification of the inserts and allowed to hybridize with single stranded plasmids of the same library. The resulting double-stranded forms were removed using streptavidin magnetic beads, the remaining single stranded plasmids were converted to double stranded molecules using Sequenase (Amersham, Arlington Hills, Ill.), and the plasmid DNA stored at −20° C. prior to transformation. Aliquots of the normalized plasmid library were used to transform *E. coli* (XLlblue or DHIOB), plated at moderate density, and the colonies picked into a 384-well master plate containing bacterial growth media using a Qbot robot (Genetix, Christchurch, UK). The clones were allowed to grow for 24 hours at 37° C. then the master plates were frozen at −80° C. for storage. The total number of colonies picked for sequencing from the normalized library was 240,000. The master plates were used to inoculate media for growth and preparation of DNA for use as template in sequencing reactions. The reactions were primarily carried out with primer that initiated at the 5' end of the cDNA inserts. However, a minor percentage of the clones were also sequenced from the 3' end. Clones were selected for 3' end sequencing based on either further biological interest or the selection of clones that could extend assemblies of contiguous sequences ("contigs") as discussed below. DNA sequencing was carried out using ABI377 automated sequencers and used either ABI FS, dirhodamine or BigDye chemistries (Applied Biosystems, Inc., Foster City, Calif.).

Analysis of sequences were done as follows: the traces generated by the automated sequencers were base-called using the program "Phred" (Gordon, Genome Res. (1998) 8:195–202), which also assigned quality values to each base. The resulting sequences were trimmed for quality in view of the assigned scores. Vector sequences were also removed. Each sequence was compared to all other fly EST sequences using the BLAST program and a filter to identify regions of near 100% identity. Sequences with potential overlap were then assembled into contigs using the programs "Phrap", "Phred" and "Consed" (Phil Green, University of Washington, Seattle, Wash.). The resulting assemblies were then compared to existing public databases and homology to known proteins was then used to direct translation of the consensus sequence. Where no BLAST homology was available, the statistically most likely translation based on codon and hexanucleotide.preference was used. The Pfam (Bateman et al., Nucleic Acids Res. (1999) 27:260–262) and Prosite (Hofmann et al., Nucleic Acids Res. (1999) 27(1) :215–219) collections of protein domains were used to identify motifs in the resulting translations. The contig sequences were archived in an Oracle-based relational database (FlyTagTm, Exelixis Pharmaceuticals, Inc., South San Francisco, Calif.).

Example 2

Assembly of VEGFR Nucleic Acid Sequence

Unless otherwise noted, the PCR conditions used for cloning the dmVEGFR nucleic acid sequence was as follows: A denaturation step of 94° C., 5 min; followed by 35 cycles of: 94° C. 1 min, 55° C. 1 min 72° C. 1 min; then, a final extension at 72° C. 10 min.

All DNA sequencing reactions were performed using standard protocols for the BigDye sequencing reagents (Applied Biosystems, Inc.) and products were analyzed using ABI 377 DNA sequencers. Trace data obtained from the ABI 377 DNA sequencers was analyzed and assembled into contigs using the Phred-Phrap programs.

Well-separated, single colonies were streaked on a plate and end-sequenced to verify the clones. Single colonies were picked and the enclosed plasmid DNA was purified using Qiagen REAL Preps (Qiagen, Inc., Valencia, Calif.). Samples were then digested with appropriate enzymes to excise insert from vector and determine size, for example the vector pOT2, (www.fruitfly.org/EST/pOT2vector.html) and can be excised with Xho1/EcoRI; or pBluescript (Stratagene) and can be excised with BssH II. Clones were then sequenced using a combination of primer walking and in vitro transposon tagging strategies.

For primer walking, primers were designed to the known DNA sequences in the clones, using the Primer-3 software (Steve Rozen, Helen J. Skaletsky (1998) Primer3). These primers were then used in sequencing reactions to extend the sequence until the full sequence of the insert was determined.

The GPS-1 Genome Priming System in vitro transposon kit (New England Biolabs, Inc., Beverly, Mass.) was used for transposon-based sequencing, following manufacturer's protocols. Briefly, multiple DNA templates with randomly interspersed primer-binding sites were generated. These clones were prepared by picking 24 colonies/clone into a Qiagen REAL Prep to purify DNA and sequenced by using supplied primers to perform bidirectional sequencing from both ends of transposon insertion. Sequences were then assembled using Phred/Phrap and analyzed using Consed. Ambiguities in the sequence were resolved by resequencing several clones. This effort resulted in 4 kilobases of sequence from the 3' end.

The 5' end of the gene was assembled by Rapid Amplification of CDNA Ends (RACE) (Frohman, PCR Methods Appl. (1994) 4:S40–58). A RACE-ready library was generated from Clontech (Palo Alto, CA) Drosophila embryo polyA+RNA (Cat# 6947–1) using Clontech's Marathon cDNA amplification kit (Cat# K1802 1), and following manufacturer's protocols. Sequences from cDNA clones, above, were used to make PCR primers for RACE reactions. All reactions were performed following manufacturer's protocols.

The RACE and sequencing results were assembled, which resulted in a contiguous nucleotide sequence of 5.3 kilobases in length, encompassing an open reading frame (ORF) of 4526 nucleotides encoding a predicted protein of 1509 amino acids. The ORF extends from base 305–4831 of SEQ ID NO:1, and encompasses 17 introns and 18 exons. The VEGFR gene region maps to 28E5–29B1 on chromosome 2, and is 18.8 kilobases long.

Further RACE and sequencing resulted in 3 additional cDNA clones. DmVEGFR78F1 as represented in SEQ ID NO:3 ; is 4.9 kilobases in length, encompassing an ORF of 4425 nucleotides encoding a predicted protein of 1475 amino acids. The ORF extends from base 1–4425 of SEQ ID NO:3. DmVEGFR10G41 as represented in SEQ ID NO:5 is 5.1 kilobases in length, encompassing an ORF of 4512 nucleotides encoding a predicted protein of 1504 amino acids. The ORF extends from base 14512 of SEQ ID NO:5. DmVEGFR4g21 as represented in SEQ ID NO:7 is 4.9 kilobases in length, encompassing an ORF of 762 nucleotides encoding a predicted protein of 253 amino acids. The ORF extends from base 1–762 of SEQ ID NO:7.

Example 3

Analysis of VEGFR Nucleic Acid Sequences

Nucleotide and amino acid sequences for each of the VEGFR nucleic acid sequences and their encoded proteins were searched against all available nucleotide and amino acid sequences in the public databases, using BLAST (Altschul et al., supra). Table 2 below summarizes the results. The 5 most similar sequences are listed.

TABLE 2

| GI# | DESCRIPTION |
|---|---|
| DNA BLAST | |
| 3041826 = AC004532.1 | *Drosophila melanogaster* DNA sequence (P1s DS03465 (D149) and DS08544 (D187)), complete sequence |
| 1705364 = AA141883 | *Drosophila melanogaster* cDNA clone CK02679 3 prime |
| 1705362 = AA141900 | *Drosophila melanogaster* cDNA clone CK02679 5 prime |
| AI533795 | *Drosophila melanogaster* Schneider L2cell culture pcDNA clone SD05757 5 prime |
| 293782 = L07297 | *Mus musculus* receptor tyrosine kinase (FLT) |
| PROTEIN BLAST | |
| 2143726 = I60598 | Fit-1 tyrosine kinase receptor - rat |
| 600379 = BAA05857 | Fit-1 tyrosine kinase receptor - *Rattus norvegicus* |
| 2137724 = I78875 | Receptor tyrosine kinase - mouse |
| 293783 = AAA40078 | Receptor tyrosine kinase - *Mus musculus* |
| 2809069 = BAA24498 | Flt-1 - *Mus musculus* |

Subsequent to the identification of these sequences, AAF52626 was deposited in the public databases. This is a predicted gene product from the genome sequence of Drosophila. Blast searches of the dmVEGFR amino acid sequences against this sequence produce the closest similarity and homology.

The BLAST analysis also revealed several other receptor tyrosine kinase proteins which share significant amino acid homology (20–50% identity; 36–74 % similarity) with various portions of the IgG-like domains of dmVEGFR. These include the mammalian VEGF receptors and their close relatives in the PDGF receptor family (Van Der,Greer and Hunter, Annu Rev Cell Biol. (1994) 10:251–337; Weissmann et al., Cell (1997) 91:695–704). BLAST results for SEQ ID NO:2 indicated 12 amino acid residues as the shortest stretch of contiguous amino acids that is novel with respect to published sequences and 20 amino acids as the shortest stretch of contiguous amino acids for which there are no sequences contained within public databases sharing 100% sequence similarity.

The Berkeley Drosophila Genome Project reported that tracheal staining in embryonic tissue was observed in in situ expression data of cDNA clone CK02679. This is consistent with the role of VEGFR in tracheal development in the insect.

Example 4

Binding Assays for Detecting Binding of Compounds to dmVEGFR

Binding assays using soluble dmVEGFR generated by cells expressing the receptors are performed essentially as described by Piossek et al. (supra). Microtiter plates are prepared by adding to each well 50 $\mu$l of soluble dmVEGFR (dmsVEGFR) prepared in PBS at a concentration of about 0.4 $\mu$g. The wells are coated for 30 minutes with shaking. Then 200 $\mu$l of 4% BSA in PBS is added for another 30 minutes. The solution is removed and the plates are washed with 0.1% BSA in PBS. 10 $\mu$g/ml of test compound in PBS with 0.1% BSA is added to each well along with 40 gl of $^{25}$I-VEGF (approx. 15,000 cpm or 300–600 pM) was added in PBS, with 0.1% BSA. The incubation mixture is shaken for 60 minutes and radioactivity is removed. After three washes with 0.1% BSA in PBS, 100 $\mu$l of 0.5% sodium dodecyl sulfate (SDS) is added and the plate is shaken for 30 minutes. Binding is determined by counting individual wells in a gamma counter. Compounds that specifically bind to dmVEGFR are tested for their ability to modulate cell proliferation as described in Example 5.

Example 5

Endothelial Cell Proliferation Assay

Stable endothelial cell lines, such as porcine aortic endothelial (PAE) expressing dmVEGFR are established as reported (Landgren et al., Oncogene (1998) 16:359–367; Joukov et al., EMBO J. (1997) 16:3898–3911) and maintained in Ham's F12 medium supplemented with penicillin/streptomycin and 10% fetal calf serum (FCS). Cells are grown in 25 cm flasks in Ham's F12 medium supplemented with 10% FCS. Cells are trypsinized and resuspended in Ham's F12 medium containing 1% FCS. Approximately $10^4$ cells are seeded in each well of 24-well plates. Compounds at various concentrations are added to the cells. After incubation for 72 h at 37° C. with 5% $CO_2$, cells are trypsinized and resuspended in Isoton II solution (Coulter, Miami, Fla.) and counted with a Coulter counter.

Example 6

Mutation Analysis of dmVEGFR Sequence

Three mutants in dmVEGFR were isolated from a transposon screen that used an engineered piggyBac (pB ) element from the cabbage looper *Trichoplusia ni* (Cary LC et al. Virology (1989) 172:156–169). The ~5 kb element contains approximately 350 bp terminal piggyBac sequences, corresponding to nucleotide (nt) 1–331 and nt 2126–2475 of gi156155, and the white minigene, which serves as a marker of transposition, flanked by direct FRT sites (GI172190, nt 676–723). the white minigene (http://flybase.bio.indiana.edu/.bin/tpseq.html?FBms0000515), which serves as a marker of transposition, flanked by direct FRT sites (GI172190, nt 676–723).

The element was introduced by standard germline transformation into pre-blastoderm embryos (Ashburner, *Drosophila: A Laboratory Handbook*, Cold Spring Harbor Laboratory Press, 1989) using a "helper plasmid," which transiently supplies the source of transposase but is unable to integrate into the host's genome. Once parental stocks had been established, subsequent germ-line mobilizations generated large numbers of progeny bearing individual insertions in different chromosomal loci.

Briefly, a first genetic cross brought together the parental pB vector and a stably integrated source of pB transposase, which was transferred to the CyO balancer chromosome in order to facilitate subsequent molecular and genetic analysis. This source of pB transposase (nucleotides 127–2475 of gi 156155) was generated under the control of the Drosophila hsp70 promoter (nucleotides, 1261–1712 of gi157720). Progeny were heat-shocked eight times during development to activate the transposase. Dysgenic male progeny that harbored both elements were recovered. Mottled eye color indicated mobilization of the vector in these animals' somatic tissue. The dysgenic animals were out-crossed in order to segregate the source of transposase from the pB vector and recover stable novel insertions, which were identified by progeny whose eye color differed from that of the parental host. Standard methods were used to map and balance these insertions. Two of the insertions resulted in mutants with altered phenotypes and one of the insertions resulted in lethality. The characterization of mutant phenotypes is currently underway. Preliminary results point to an altered tracheal phenotype.

What is claimed is:

1. A purified polypeptide comprising an amino acid sequence as set forth in SEQ ID NO:2.

2. An isolated nucleic acid molecule of less than about 20 kb in size comprising a nucleic acid sequercz that encodes a polypeptide comprising an amino acid sequence as set forth in SEQ ID NO:2.

3. A vector comprising the nucleic acid molecule of claim 2.

4. A host cell comprising the vector of claim 3.

5. A process for producing a dmVEGFR protein comprising culturing the host cell of claim 4 under conditions suitable for expression of said dmVEGFR protein and recovering said protein.

* * * * *

SEQUENCE LISTING

```
<160> NUMBER OF SEQ ID NOS: 8

<210> SEQ ID NO 1
<211> LENGTH: 5220
<212> TYPE: DNA
<213> ORGANISM: Drosophila melanogaster

<400> SEQUENCE: 1

tcgagctgta cggacgtcaa agcggaagaa aatttcgcgg gcttttgact tgtgttcggt     60

gcaaactgtt caaactttgc cgacgacgca gtatttattg tctttcaaga gcaaccgata    120

ctgctgaagt gccccacgca gaaagtgtta agcacagaaa accacaactg caacgctaag    180

tgagcaaagt gtctttcagc gtgaccatgg cattaaaggg ccaaatgtgt taaaattgtg    240

aatatttaag agtgtaaaat tagcacaata tataatcgca aaggaaacaa actaaccaag    300

ccatatggcg atgcttcccc ggttgattct gctgcccctg ctcctgattt tgcggatctc    360

gtggagcgat gctgtgcctt tgcagcagtt ctcaccggat cccgatgaca gcatcgagaa    420

ctgcggcggc gagaatggag ctcccctgat gacgccctgc aagagcgcca ttatcctgga    480

tgcccagacg agcaccacgc taaagtgcga agacgacgag ccgatgagct ggtggaccag    540

tcaatcgcaa tatgtgcatg taaagtcctt cgataatacg gaggatccgg ctcgaccatt    600

cggaactagc ctgcatctca tcgaagtgac ggctgactat gtggcagcct actattgcgt    660

gaagacttcg aaattcagtc agatcgccaa ggaggagcag tcggacgagg cgatgatcga    720

attggttaat caaggatacg ccagctccat ctacgtgtac gtgaatgatc cggatactaa    780

gctggtcgat agtcataacg tggtgacagc acgccagtat accgacgtag tcataccctg    840

taaaccagcc atgccggaca cagaggtgct gctagagacc agtaatggag aaagcacgtg    900

gaaaatcagc tcgaaaggtc agattcaggg taaccccaag ttcttcgata gtgtgaggta    960

ccaccccaga tggggcttta cctttcgagt cattgactgt gtatccggtt acttgtattg   1020

caaaacgttg gactatgaat tgatcattga cgttacctat ccagaaaaag acggcaaacc   1080

gctgccaaag cccgtgatca ggtcctccgt ggagcatcac gtcttcacgg acaccaactt   1140
```

-continued

```
caccctggat tgcgagcagt ccgcctacgt tgaatcagta tacggaatgg aatggttcac   1200
tccgtcccgg gatgagaatc gcatatttgc ctcccaatca agaaccgatc ccaagaccag   1260
gaacagcacc caccagacgg gcaggagcac cttgacagtg ctaaatgcac aaccctcgga   1320
cactggtcta tacaagtgtg tgaccacaga taattctaac cagaacgtac aacgtgccac   1380
ctacaggatt aaggtgctaa agcaaaacga aagttacctg aacgtgggcg aaccatcggg   1440
tcattacaac gttcaggaat atgccaatcg cacgatccaa atgaccgcga actttgaggg   1500
atttccgacg ccctccttca gttggttcaa acccgatggc accgaggtgc gacaatcgga   1560
gaataacttc aagattctct ccacggaatt gagcacaatg ctccaggtgc tgaacgccca   1620
attgcaggac agtggcacgt atgtcctccg tggatccaat tccttcggcg tcgttcagcg   1680
ggagtacaac gtcagtgtga tggacgcacc ggcgctgaag atgtcggacg cctatgtcca   1740
ggtgggatcc gtggcgcgac tggagtgtac agtacgctcc tatccgccgg ctatcgtgac   1800
cttcttcttc cgcccctgca gcctggaacc acagtggccc acttgctccg tgctcaatca   1860
gaactttagc ttgccgagtg aacaggagaa atatcagttc cagacccggc cgagaccagg   1920
aaagttgagt gtggaacgca tatacgaggt atccttcctg cccacagagc cgggaatcct   1980
tacgtgcatt gcccaaaata tcattgatgg aaaggaacga agaaccctga cgaaggcgca   2040
cgttctgctg ggcaacattt ccgagaacat gaccatatat ggcttcgata aggatcacaa   2100
aatcgccaag gaggacaatg tgaacttcac ctgcgaggcg ttggcctatc acttcgatgg   2160
aaatcttaaa tggttcatca acggagagga tttaaaggag tcggattcgg ttcacattga   2220
gaccagccat accaagtact cctacaagag cactgtacac atcacaacga tatccgacag   2280
ggatcgtgga acctatgagt gccgggccta ccacaacgac aaggatgccg tttacagcag   2340
ccgggagata gacttgtacg tccacgatcc ctctgctcct cagtggacaa acggcggaca   2400
ggagggtcac tcgaaaataa agcgcaaact aagccaaacg ctggagctgg agtgtgcctc   2460
cacagcggtt cccgtggcaa ttgtgcgttg gtttaaggac gacaaggagg tgaccgaatc   2520
aaagctcagg cacatcattg aaaaggaatc caagctgctg atcactcacc tgtatcccgg   2580
agatgaaggc gtctacaagt gtgtggtgga gaaccgattg gacagaatcg aacgctcctt   2640
cacggtagtg atatcagatc tgcccggcat tagcatggcc tgggtgtggt tcggtgtgat   2700
actattcctc atcctgatcg gtctgtgcgt cttcctcgcc gtgcgctacc agaaggagca   2760
caagcggcat ctggccctta aggctgccgg attggccaac ttcgaggagg gcgccgtggg   2820
acacatcaat cccgatctga ccctggacga gcaggcggaa ctgctgccct acaatcggga   2880
attcgagttc ccacgggaaa acctgaaact gggcaagcaa ctgggagccg gagcatttgg   2940
cgtggtgctc aagggcgagg ccaagggcat ccggcgagag gagcccacca ccacggtggc   3000
cgtcaaaatg gtcaaggcga cggctgacaa cgaggtggtg cgggcactgg tctccgagct   3060
caagatcatg gtacatctgg gacagcactt gaatgtggtc aatctcctgg gtgcagttac   3120
caaaaatatt gcgaagcgcg aactaatggt cattgtggaa tactgtcgct ttggcaacat   3180
acagaacttc cttctgagga acagaaagtg ttttatcaat caaatcaatc cagacaccga   3240
tcacattgac cccagcatca tgacccagcg catgtccgac aactacgaac tgcaccgcga   3300
tacgaatggt ggtggcttga agtacgccaa tgtcggtttc ccgatccact cttacattaa   3360
tgagccgcac aacaataaca cgcaaccgcc aactcatcgc agaaactcgg acaatgatcc   3420
ccgatcggga acccgagccg gacgaaccgg atccggaaca gccacctaca gctacgaccg   3480
tcagatggat acctgtgcca ccgtaatgac caccgtccca gaagacgatc aaataatgtc   3540
```

-continued caataactcc gtacaacccg cctggcgttc caattacaaa accgactcca cggaagcgat   3600
gacagtgacc actgtggatt tgattagttg ggcattccaa gtggcaaggg gcatggatta   3660
cttgtcctcc aagaaggtgt tgcacggcga tctggccgct agaaatattc tcctctgcga   3720
ggacaatgtg gtaaagattt gtgactttgg tctggcacga tccatgtatc gaggtgataa   3780
ctacaagaag tcagagaatg gcaaattgcc catcaagtgg ctggcgctgg aatcgctgag   3840
cgatcatgtg ttcagcacat acagcgatgt ttggtcctac ggaattgttc tatgggagat   3900
gttctcgctg gccaaggtgc cgtatccggg catcgatccc aaccaggagc tatttaacaa   3960
actgaacgat ggctaccgca tggagaagcc gaaatttgcc aaccaggagc tctacgagat   4020
tatgctagag tgctggcgaa agaatcccga gagcagacct ttgtttgctg agctggaaaa   4080
gcgatttgca aacatgctgg gcgaggatgt agccagccac tacctggacc taaacaatcc   4140
gtacatgcag agcaacattg agtacatgaa gaagcagtct acggattacc tggcactgat   4200
gggctcaccc gacgaactgg cgcctgcagc tccgcgctac gtgaatgggc acatagtgcc   4260
cgatatacgc atcgaagagc taccggatga ctacatggag atgagccggg actctgatcc   4320
cgatgcctgc accgccatat tctcacccac acgcctcgag ggcgagtcct cagactttcc   4380
ggatttctct agcgaaacca ctttcaattt cccaggggcg cgacagtcgc ctacgctgag   4440
taacaatctc aacagcggat cgagtaagcc gctccgcaag aagaacggca tgccaactgt   4500
ggatgtggcg gatcaggcgc cggaggagat acctatgctg catcgcagct ccactggatc   4560
ggatggaagt ccggaacagg gaaggcgctt caatcaggcc cttaagcagc agtatgtcac   4620
gcccacaccg tcccctcgcc atcatgtgga gaccaaactc aatggggagc catccgaaaa   4680
ctatgtgaat atgaagccac cgaggaagaa tatacccggc aaaaccacaa caggtggcgg   4740
gggtgctgct gctggtgcct ccacggaggc cttctcgaat cccagctacc agccactgtc   4800
caccgtcaac gagaaggagc aacgaaggta ttaggacgtc ccggagccat tagattaagt   4860
ttaggacctc tttgcagctc agttggagtt ttaagtgaaa tattaaatag aaaattttaa   4920
atattgtata atccacttat gtaatgacta ttgttgatct taggaaaaca aattgttaac   4980
agaaagtaat cgtacgcgat ataacctttt aaaaaaaaaa gttaaaattt caacttaatt   5040
gtttaggggc ctttaagaaa caatactact tagtggcatt gttaagattc tgatatagct   5100
ttaggaccac acactcactc catgttatat actattaatg ccatttcatg ttttacattt   5160
agtgtactct aagtcgatta aacttatcta tgtaaatgat tgtcttgaat tgtgtatgca   5220

<210> SEQ ID NO 2
<211> LENGTH: 1509
<212> TYPE: PRT
<213> ORGANISM: Drosophila melanogaster

<400> SEQUENCE: 2

Met Ala Met Leu Pro Arg Leu Ile Leu Leu Pro Leu Leu Leu Ile Leu
1               5                   10                  15

Arg Ile Ser Trp Ser Asp Ala Val Pro Leu Gln Gln Phe Ser Pro Asp
            20                  25                  30

Pro Asp Asp Ser Ile Glu Asn Cys Gly Gly Glu Asn Gly Ala Pro Leu
        35                  40                  45

Met Thr Pro Cys Lys Ser Ala Ile Ile Leu Asp Ala Gln Thr Ser Thr
    50                  55                  60

Thr Leu Lys Cys Glu Asp Asp Glu Pro Met Ser Trp Trp Thr Ser Gln
65                  70                  75                  80

-continued

```
Ser Gln Tyr Val His Val Lys Ser Phe Asp Asn Thr Glu Asp Pro Ala
                85                  90                  95

Arg Pro Phe Gly Thr Ser Leu His Leu Ile Glu Val Thr Ala Asp Tyr
            100                 105                 110

Val Ala Ala Tyr Tyr Cys Val Lys Thr Ser Lys Phe Ser Gln Ile Ala
        115                 120                 125

Lys Glu Glu Gln Ser Asp Glu Ala Met Ile Glu Leu Val Asn Gln Gly
    130                 135                 140

Tyr Ala Ser Ser Ile Tyr Val Tyr Val Asn Asp Pro Asp Thr Lys Leu
145                 150                 155                 160

Val Asp Ser His Asn Val Val Thr Ala Arg Gln Tyr Thr Asp Val Val
                165                 170                 175

Ile Pro Cys Lys Pro Ala Met Pro Asp Thr Glu Val Leu Leu Glu Thr
            180                 185                 190

Ser Asn Gly Glu Ser Thr Trp Lys Ile Ser Ser Lys Gly Gln Ile Gln
        195                 200                 205

Gly Asn Pro Lys Phe Phe Asp Ser Val Arg Tyr His Pro Arg Trp Gly
    210                 215                 220

Phe Thr Phe Arg Val Ile Asp Cys Val Ser Gly Tyr Leu Tyr Cys Lys
225                 230                 235                 240

Thr Leu Asp Tyr Glu Leu Ile Ile Asp Val Thr Tyr Pro Glu Lys Asp
                245                 250                 255

Gly Lys Pro Leu Pro Lys Pro Val Ile Arg Ser Ser Val Glu His His
            260                 265                 270

Val Phe Thr Asp Thr Asn Phe Thr Leu Asp Cys Glu Gln Ser Ala Tyr
        275                 280                 285

Val Glu Ser Val Tyr Gly Met Glu Trp Phe Thr Pro Ser Arg Asp Glu
    290                 295                 300

Asn Arg Ile Phe Ala Ser Gln Ser Arg Thr Asp Pro Lys Thr Arg Asn
305                 310                 315                 320

Ser Thr His Gln Thr Gly Arg Ser Thr Leu Thr Val Leu Asn Ala Gln
                325                 330                 335

Pro Ser Asp Thr Gly Leu Tyr Lys Cys Val Thr Thr Asp Asn Ser Asn
            340                 345                 350

Gln Asn Val Gln Arg Ala Thr Tyr Arg Ile Lys Val Leu Lys Gln Asn
        355                 360                 365

Glu Ser Tyr Leu Asn Val Gly Glu Pro Ser Gly His Tyr Asn Val Gln
    370                 375                 380

Glu Tyr Ala Asn Arg Thr Ile Gln Met Thr Ala Asn Phe Glu Gly Phe
385                 390                 395                 400

Pro Thr Pro Ser Phe Ser Trp Phe Lys Pro Asp Gly Thr Glu Val Arg
                405                 410                 415

Gln Ser Glu Asn Asn Phe Lys Ile Leu Ser Thr Glu Leu Ser Thr Met
            420                 425                 430

Leu Gln Val Leu Asn Ala Gln Leu Gln Asp Ser Gly Thr Tyr Val Leu
        435                 440                 445

Arg Gly Ser Asn Ser Phe Gly Val Val Gln Arg Glu Tyr Asn Val Ser
    450                 455                 460

Val Met Asp Ala Pro Ala Leu Lys Met Ser Asp Ala Tyr Val Gln Val
465                 470                 475                 480

Gly Ser Val Ala Arg Leu Glu Cys Thr Val Arg Ser Tyr Pro Pro Ala
                485                 490                 495
```

-continued

```
Ile Val Thr Phe Phe Phe Arg Pro Cys Ser Leu Glu Pro Gln Trp Pro
            500                 505                 510

Thr Cys Ser Val Leu Asn Gln Asn Phe Ser Leu Pro Ser Glu Gln Glu
        515                 520                 525

Lys Tyr Gln Phe Gln Thr Arg Pro Arg Pro Gly Lys Leu Ser Val Glu
    530                 535                 540

Arg Ile Tyr Glu Val Ser Phe Leu Pro Thr Glu Pro Gly Ile Leu Thr
545                 550                 555                 560

Cys Ile Ala Gln Asn Ile Ile Asp Gly Lys Glu Arg Arg Thr Leu Thr
                565                 570                 575

Lys Ala His Val Leu Leu Gly Asn Ile Ser Glu Asn Met Thr Ile Tyr
            580                 585                 590

Gly Phe Asp Lys Asp His Lys Ile Ala Lys Glu Asp Asn Val Asn Phe
        595                 600                 605

Thr Cys Glu Ala Leu Ala Tyr His Phe Asp Gly Asn Leu Lys Trp Phe
    610                 615                 620

Ile Asn Gly Glu Asp Leu Lys Glu Ser Asp Ser Val His Ile Glu Thr
625                 630                 635                 640

Ser His Thr Lys Tyr Ser Tyr Lys Ser Thr Val His Ile Thr Thr Ile
                645                 650                 655

Ser Asp Arg Asp Arg Gly Thr Tyr Glu Cys Arg Ala Tyr His Asn Asp
            660                 665                 670

Lys Asp Ala Val Tyr Ser Ser Arg Glu Ile Asp Leu Tyr Val His Asp
        675                 680                 685

Pro Ser Ala Pro Gln Trp Thr Asn Gly Gly Gln Glu Gly His Ser Lys
    690                 695                 700

Ile Lys Arg Lys Leu Ser Gln Thr Leu Glu Leu Glu Cys Ala Ser Thr
705                 710                 715                 720

Ala Val Pro Val Ala Ile Val Arg Trp Phe Lys Asp Asp Lys Glu Val
                725                 730                 735

Thr Glu Ser Lys Leu Arg His Ile Ile Glu Lys Glu Ser Lys Leu Leu
            740                 745                 750

Ile Thr His Leu Tyr Pro Gly Asp Glu Gly Val Tyr Lys Cys Val Val
        755                 760                 765

Glu Asn Arg Leu Asp Arg Ile Glu Arg Ser Phe Thr Val Val Ile Ser
    770                 775                 780

Asp Leu Pro Gly Ile Ser Met Ala Trp Val Trp Phe Gly Val Ile Leu
785                 790                 795                 800

Phe Leu Ile Leu Ile Gly Leu Cys Val Phe Leu Ala Val Arg Tyr Gln
                805                 810                 815

Lys Glu His Lys Arg His Leu Ala Leu Lys Ala Ala Gly Leu Ala Asn
            820                 825                 830

Phe Glu Glu Gly Ala Val Gly His Ile Asn Pro Asp Leu Thr Leu Asp
        835                 840                 845

Glu Gln Ala Glu Leu Leu Pro Tyr Asn Arg Glu Phe Glu Phe Pro Arg
    850                 855                 860

Glu Asn Leu Lys Leu Gly Lys Gln Leu Gly Ala Gly Ala Phe Gly Val
865                 870                 875                 880

Val Leu Lys Gly Glu Ala Lys Gly Ile Arg Arg Glu Glu Pro Thr Thr
                885                 890                 895

Thr Val Ala Val Lys Met Val Lys Ala Thr Ala Asp Asn Glu Val Val
            900                 905                 910

Arg Ala Leu Val Ser Glu Leu Lys Ile Met Val His Leu Gly Gln His
```

-continued

```
        915                 920                 925

Leu Asn Val Val Asn Leu Leu Gly Ala Val Thr Lys Asn Ile Ala Lys
    930                 935                 940

Arg Glu Leu Met Val Ile Val Glu Tyr Cys Arg Phe Gly Asn Ile Gln
945                 950                 955                 960

Asn Phe Leu Leu Arg Asn Arg Lys Cys Phe Ile Asn Gln Ile Asn Pro
                965                 970                 975

Asp Thr Asp His Ile Asp Pro Ser Ile Met Thr Gln Arg Met Ser Asp
            980                 985                 990

Asn Tyr Glu Leu His Arg Asp Thr  Asn Gly Gly Gly Leu  Lys Tyr Ala
        995                 1000                1005

Asn Val  Gly Phe Pro Ile His  Ser Tyr Ile Asn Glu  Pro His Asn
    1010                 1015                 1020

Asn Asn  Thr Gln Pro Pro Thr  His Arg Arg Asn Ser  Asp Asn Asp
    1025                 1030                 1035

Pro Arg  Ser Gly Thr Arg Ala  Gly Arg Thr Gly Ser  Gly Thr Ala
    1040                 1045                 1050

Thr Tyr  Ser Tyr Asp Arg Gln  Met Asp Thr Cys Ala  Thr Val Met
    1055                 1060                 1065

Thr Thr  Val Pro Glu Asp Asp  Gln Ile Met Ser Asn  Asn Ser Val
    1070                 1075                 1080

Gln Pro  Ala Trp Arg Ser Asn  Tyr Lys Thr Asp Ser  Thr Glu Ala
    1085                 1090                 1095

Met Thr  Val Thr Thr Val Asp  Leu Ile Ser Trp Ala  Phe Gln Val
    1100                 1105                 1110

Ala Arg  Gly Met Asp Tyr Leu  Ser Ser Lys Lys Val  Leu His Gly
    1115                 1120                 1125

Asp Leu  Ala Ala Arg Asn Ile  Leu Leu Cys Glu Asp  Asn Val Val
    1130                 1135                 1140

Lys Ile  Cys Asp Phe Gly Leu  Ala Arg Ser Met Tyr  Arg Gly Asp
    1145                 1150                 1155

Asn Tyr  Lys Lys Ser Glu Asn  Gly Lys Leu Pro Ile  Lys Trp Leu
    1160                 1165                 1170

Ala Leu  Glu Ser Leu Ser Asp  His Val Phe Ser Thr  Tyr Ser Asp
    1175                 1180                 1185

Val Trp  Ser Tyr Gly Ile Val  Leu Trp Glu Met Phe  Ser Leu Ala
    1190                 1195                 1200

Lys Val  Pro Tyr Pro Gly Ile  Asp Pro Asn Gln Glu  Leu Phe Asn
    1205                 1210                 1215

Lys Leu  Asn Asp Gly Tyr Arg  Met Glu Lys Pro Lys  Phe Ala Asn
    1220                 1225                 1230

Gln Glu  Leu Tyr Glu Ile Met  Leu Glu Cys Trp Arg  Lys Asn Pro
    1235                 1240                 1245

Glu Ser  Arg Pro Leu Phe Ala  Glu Leu Glu Lys Arg  Phe Ala Asn
    1250                 1255                 1260

Met Leu  Gly Glu Asp Val Ala  Ser His Tyr Leu Asp  Leu Asn Asn
    1265                 1270                 1275

Pro Tyr  Met Gln Ser Asn Ile  Glu Tyr Met Lys Lys  Gln Ser Thr
    1280                 1285                 1290

Asp Tyr  Leu Ala Leu Met Gly  Ser Pro Asp Glu Leu  Ala Pro Ala
    1295                 1300                 1305

Ala Pro  Arg Tyr Val Asn Gly  His Ile Val Pro Asp  Ile Arg Ile
    1310                 1315                 1320
```

-continued

```
Glu Glu  Leu Pro Asp Asp Tyr  Met Glu Met Ser Arg  Asp Ser Asp
    1325                1330                1335

Pro Asp  Ala Cys Thr Ala Ile  Phe Ser Pro Thr Arg  Leu Glu Gly
    1340                1345                1350

Glu Ser  Ser Asp Phe Pro Asp  Phe Ser Ser Glu Thr  Thr Phe Asn
    1355                1360                1365

Phe Pro  Gly Ala Arg Gln Ser  Pro Thr Leu Ser Asn  Asn Leu Asn
    1370                1375                1380

Ser Gly  Ser Ser Lys Pro Leu  Arg Lys Lys Asn Gly  Met Pro Thr
    1385                1390                1395

Val Asp  Val Ala Asp Gln Ala  Pro Glu Glu Ile Pro  Met Leu His
    1400                1405                1410

Arg Ser  Ser Thr Gly Ser Asp  Gly Ser Pro Glu Gln  Gly Arg Arg
    1415                1420                1425

Phe Asn  Gln Ala Leu Lys Gln  Gln Tyr Val Thr Pro  Thr Pro Ser
    1430                1435                1440

Pro Arg  His His Val Glu Thr  Lys Leu Asn Gly Glu  Pro Ser Glu
    1445                1450                1455

Asn Tyr  Val Asn Met Lys Pro  Pro Arg Lys Asn Ile  Pro Gly Lys
    1460                1465                1470

Thr Thr  Thr Gly Gly Gly Gly  Ala Ala Ala Gly Ala  Ser Thr Glu
    1475                1480                1485

Ala Phe  Ser Asn Pro Ser Tyr  Gln Pro Leu Ser Thr  Val Asn Glu
    1490                1495                1500

Lys Glu  Gln Arg Arg Tyr
    1505

<210> SEQ ID NO 3
<211> LENGTH: 4890
<212> TYPE: DNA
<213> ORGANISM: Drosophila melanogaster

<400> SEQUENCE: 3

atggcgatgc ttccgcggtt gattctgctg ccactgctcc tgattttgcg gatctcgtgg     60

agcgatgctg tgcctttgca gcagttctca ccggatcccg atgacagcat cgagaactgc    120

ggcggcgaga atggagctcc cctgatgacg ccctgcaaga gcgccattat cctggatgcc    180

cagacgagca ccacgcttaa gtgcgaggac gacgagccga tgagctggtg gaccagtcaa    240

tcgcaatatg tgcatgtgaa gtccttcgat aatacggagg atccggctcg accattcgga    300

actagcctgc atctcatcga agtgacggct gactatgtgg cagcctacta ttgcgtgaag    360

acttcgaaat tcagtcagat cgccaaggag gagcagtcgg acgaggcgat gatcgaattg    420

gttaatcaag gatacgccag ctccatctac gtgtacgtga atgatccgga cactaagctg    480

gtcgatagtc ataacgtggt gacggcacgc cagtataccg acgtagtcat accctgtaaa    540

ccagccatgc cggacacaga ggtgctgcta gagaccagta atggagaaat gcattccagc    600

aaatctgtcg gtcgatacga tccgcaacgg ggattcacca tcgaaatccg aagcatcgtg    660

gatggcggag actactactg ccgacccaat ccgccattcc cgcataacga agaggagatg    720

accagcatag aagtgcgctt tattggtaac ggtcacattg ataaagacgg caaaccgctg    780

ccaaagcccg tgatcaggtc ctccgtggag catcacgtct tcacggacac caacttcacc    840

ctggattgcg agcagtccgc ctacgttgaa tcagtatacg gaatggaatg gttcactccg    900

tcccgggatg agaatcgcat atttgcctcc caatcaagaa ccgatcccaa gaccaggaac    960
```

-continued

```
agcacccatc agacgggcag gagcaccttg acagtgctaa atgcacaacc ctcggacact   1020
ggtctataca agtgtgtgac aacagataat tctaaccaga acgtacaacg tgccacctac   1080
aggattaagg tgctaaagca aaacgaaagt tacctgaacg tgggcgaacc atcgggtcat   1140
tacaacgttc aggaatatgc caatcgcacg atccaaatga ccgcgaactt tgagggattt   1200
ccgacgccct ccttcagttg gttcaaaccc gatggcaccg aggtgcgaca atcggagaat   1260
aacttcaaga ttctctccac ggaattgagc acaatgctcc aggtgctgaa cgcccaattg   1320
caggacagcg gcacgtatgt cctccgtgga tccaattcct tcggcgtcgt tcagcgggag   1380
tacaacgtca gtgtgatgga cgcaccggcg ctgaagatgt cggacgccta tgtccaggtg   1440
ggatccgtgg cgcgactgga gtgcacagta cgctcctatc cgccggctat cgtgaccttc   1500
ttcttccgcc cctgcagcct ggaaccacag tggcccactt gctctgtgct caatcagaac   1560
tttagcttgc cgagtgaaca ggagaaatat cagttccaga cccggcccag acccggaaag   1620
ctgagtgtgg aacgcatata cgaggtatcc ttcctgccca cggagccggg aatcctcaca   1680
tgcattgccc aaaatatcat tgatggaaag gaacgaagaa ccctgacgaa ggcgcacgtt   1740
ctgctgggca acatttccga gaacatgacc atatatggct tcgataagga tcacaaaatc   1800
gccaaggagg acaatgtgaa cttcacctgc gaggcgctgg cctatcactt cgatggaaat   1860
cttaaatggt tcatcaatgg agaggatttg aaggagtcgg attcggttca cattgagacc   1920
agccatacca agtactccta caagagcact gtacacatca caacgatatc cgacagggat   1980
cgtggaacct atgagtgccg ggcctaccac aacgacaagg atgccgttta cagcagccgg   2040
gagatagact tgtacgtcca cgatccctct gctcctcagt ggacaaacgg cggacaggag   2100
ggtcactcga aaataaagcg caaactaagc caaacgctgg agctggagtg tgcctccaca   2160
gcggttcccg tggcaattgt gcgttggttt aaggacgaca aggaagtgac cgaatcaaag   2220
ctcaggcaca tcattgaaaa ggaatccaag ctgctgatca ctcacctgta tcccggagat   2280
gaaggcgtct acaagtgtgt ggtggagaac cgattggaca gaatcgaacg ctccttcacg   2340
gtagtgatat cagatctgcc cggcattagc atggcctggg tgtggttcgg tgtgatacta   2400
ttcctcatcc tgatcggtct gtgcgtcttc ctcgccgtgc gctaccagaa ggagcacaag   2460
cggcatctgg cccttaaggc agccggattg gccaacttcg aggagggcgc cgtgggacac   2520
atcaatcccg atctgaccct ggacgagcag gcggaactgc tgccctacaa tcgggaattc   2580
gagttcccac gggaaaacct gaaactgggc aagcaactcg gagccggagc atttggcgtt   2640
gtgctcaagg gcgaggccaa gggcatccgg cgagaggagc ccaccaccac ggtggccgtc   2700
aaaatggtca aggcgacggc tgacaacgag gtggtgcggg cactggtctc cgagctcaag   2760
atcatggtac atctgggaca gcacttgaat gtggtcaatc tcctgggtgc agttaccaaa   2820
aatattgcga agcgcgaact aatggtcatt gtggaatact gtcgctttgg caacatacag   2880
aacttccttc tgaggaacag aaagtgcttt atcaatcaaa tcaatccaga caccgatcac   2940
attgacccca gcatcataac ccagcgcatg tccgacaact acgaactgca ccgaaattcg   3000
gacaatgatc cccgatcggg cacccgagcc ggacgaaccg gatccggaac agccacctac   3060
agctacgacc gtcagatgga tacctgtgcc accgtaatga ccaccgtccc agaagacgat   3120
caaataatgt ccaataactc cgtacaaccc gcctggcgtt ccaattacaa aaccgactcc   3180
acggaggcga tgacagtgac cactgtggat ttgatcagtt gggcattcca agtggcaagg   3240
ggcatggatt acttgtcctc caagaaggtg ttgcacggcg atctggccgc tagaaatatt   3300
```

-continued

```
ctcctctgcg aggacaatgt ggtaaagatt tgtgactttg gtctggctcg atccatgtat   3360

cgaggtgata actacaagaa gtcagagaat ggcaaattgc ccatcaagtg gctggcgctg   3420

gaatcgctga gcgatcatgt gttcagcaca tacagcgatg tttggtccta cggaattgtt   3480

ctatgggaga tgttctcgct ggccaaggtg ccgtatccgg gcatcgatcc caaccaagag   3540

ctatttaaca aactgaacga tggctaccgc atggagaagc cgaaatttgc caaccaggag   3600

ctctacgaga ttatgctaga gtgctggcga aagaatcccg agagcagacc tttgtttgct   3660

gagctggaga agcgatttgc aaacatgctg ggcgaggatg tagccagcca ctgcctggac   3720

ctaaacaatc cgtacatgca gagcaacatt gagtacatga agaagcagtc tacggattac   3780

ctggcactga tgggatcacc cgacgagctg gcgcctgcag ctccgcgcta cgtgaacggg   3840

cacatagtgc ccgatatacg catcgaagag ctgccggatg actacatgga gatgagccgg   3900

gattctgatc ccgatgcctg caccgccata ttctcaccca cacgcctcga gggcgagtcc   3960

tcagactttc cggatttctc tagcgaaacc actttcaatt tcccaggggc gcgacagtcg   4020

cctacgctga gtaacaatct caacagcgga tcgagtaagc cgctccgcaa gaagaacggc   4080

atgccaactg tggatgtggc agatcaggcg ccggaggaga tacctatgct gcatcgcagc   4140

tccactggat cggatggaag tccggaacag ggaaggcgct tcaatcaggc ccttaagcag   4200

cagtatgtca cgcccacacc gtcccctcgc catcatgtgg agaccaaact caatggggag   4260

ccatccgaaa actatgtgaa tatgaagcca cccaggaaga atatacccgg caaaaccaca   4320

acaggtggcg gggtgctgc tgctggagcc tccacggagg ccttctcgaa tcccagctac   4380

cagccactgt ccaccgtcaa cgagaaggag caacgaaggt attaggacgt cccggagcca   4440

ttagattaag tttaggacct ctttgcagct cagttggagt tttaagtgaa atcttaaata   4500

gaaaatttta aatattgtat aatcaactta tgtaatgact attgttgatc ttaggaaaac   4560

aaattgttaa cagaaagtaa tcgtacgcga tataaccttt taaaaaaaag ttaaaatttc   4620

aacttaattg tttaggggcc tttaagaaac aatactactt agtggcattg ttaagattct   4680

gatatagctt taggaccaca cactcactcc atgttatata ctattaatgc catttcatgt   4740

tttacattta gtgtagtcta agtcgattaa acttatctat gtaaatgatt gtcttgaatt   4800

gtgtatgcat gtacctacga ctactcaaat acaatgggta tgataacaaa aaaaaaaaaa   4860

aaaaaaaaaa aaaaaaaaaa aaaaaaaaaa                                    4890
```

```
<210> SEQ ID NO 4
<211> LENGTH: 1474
<212> TYPE: PRT
<213> ORGANISM: Drosophila melanogaster

<400> SEQUENCE: 4

Met Ala Met Leu Pro Arg Leu Ile Leu Leu Pro Leu Leu Leu Ile Leu
1               5                   10                  15

Arg Ile Ser Trp Ser Asp Ala Val Pro Leu Gln Gln Phe Ser Pro Asp
            20                  25                  30

Pro Asp Asp Ser Ile Glu Asn Cys Gly Gly Glu Asn Gly Ala Pro Leu
        35                  40                  45

Met Thr Pro Cys Lys Ser Ala Ile Ile Leu Asp Ala Gln Thr Ser Thr
    50                  55                  60

Thr Leu Lys Cys Glu Asp Asp Glu Pro Met Ser Trp Trp Thr Ser Gln
65                  70                  75                  80

Ser Gln Tyr Val His Val Lys Ser Phe Asp Asn Thr Glu Asp Pro Ala
                85                  90                  95
```

-continued

```
Arg Pro Phe Gly Thr Ser Leu His Leu Ile Glu Val Thr Ala Asp Tyr
            100                 105                 110

Val Ala Ala Tyr Tyr Cys Val Lys Thr Ser Lys Phe Ser Gln Ile Ala
        115                 120                 125

Lys Glu Glu Gln Ser Asp Glu Ala Met Ile Glu Leu Val Asn Gln Gly
    130                 135                 140

Tyr Ala Ser Ser Ile Tyr Val Tyr Val Asn Asp Pro Asp Thr Lys Leu
145                 150                 155                 160

Val Asp Ser His Asn Val Val Thr Ala Arg Gln Tyr Thr Asp Val Val
                165                 170                 175

Ile Pro Cys Lys Pro Ala Met Pro Asp Thr Glu Val Leu Leu Glu Thr
            180                 185                 190

Ser Asn Gly Glu Met His Ser Ser Lys Ser Val Gly Arg Tyr Asp Pro
        195                 200                 205

Gln Arg Gly Phe Thr Ile Glu Ile Arg Ser Ile Val Asp Gly Gly Asp
    210                 215                 220

Tyr Tyr Cys Arg Pro Asn Pro Pro Phe Pro His Asn Glu Glu Glu Met
225                 230                 235                 240

Thr Ser Ile Glu Val Arg Phe Ile Gly Asn Gly His Ile Asp Lys Asp
                245                 250                 255

Gly Lys Pro Leu Pro Lys Pro Val Ile Arg Ser Ser Val Glu His His
            260                 265                 270

Val Phe Thr Asp Thr Asn Phe Thr Leu Asp Cys Glu Gln Ser Ala Tyr
        275                 280                 285

Val Glu Ser Val Tyr Gly Met Glu Trp Phe Thr Pro Ser Arg Asp Glu
    290                 295                 300

Asn Arg Ile Phe Ala Ser Gln Ser Arg Thr Asp Pro Lys Thr Arg Asn
305                 310                 315                 320

Ser Thr His Gln Thr Gly Arg Ser Thr Leu Thr Val Leu Asn Ala Gln
                325                 330                 335

Pro Ser Asp Thr Gly Leu Tyr Lys Cys Val Thr Thr Asp Asn Ser Asn
            340                 345                 350

Gln Asn Val Gln Arg Ala Thr Tyr Arg Ile Lys Val Leu Lys Gln Asn
        355                 360                 365

Glu Ser Tyr Leu Asn Val Gly Glu Pro Ser Gly His Tyr Asn Val Gln
    370                 375                 380

Glu Tyr Ala Asn Arg Thr Ile Gln Met Thr Ala Asn Phe Glu Gly Phe
385                 390                 395                 400

Pro Thr Pro Ser Phe Ser Trp Phe Lys Pro Asp Gly Thr Glu Val Arg
                405                 410                 415

Gln Ser Glu Asn Asn Phe Lys Ile Leu Ser Thr Glu Leu Ser Thr Met
            420                 425                 430

Leu Gln Val Leu Asn Ala Gln Leu Gln Asp Ser Gly Thr Tyr Val Leu
        435                 440                 445

Arg Gly Ser Asn Ser Phe Gly Val Val Gln Arg Glu Tyr Asn Val Ser
    450                 455                 460

Val Met Asp Ala Pro Ala Leu Lys Met Ser Asp Ala Tyr Val Gln Val
465                 470                 475                 480

Gly Ser Val Ala Arg Leu Glu Cys Thr Val Arg Ser Tyr Pro Pro Ala
                485                 490                 495

Ile Val Thr Phe Phe Phe Arg Pro Cys Ser Leu Glu Pro Gln Trp Pro
            500                 505                 510
```

-continued

```
Thr Cys Ser Val Leu Asn Gln Asn Phe Ser Leu Pro Ser Glu Gln Glu
        515                 520                 525

Lys Tyr Gln Phe Gln Thr Arg Pro Arg Pro Gly Lys Leu Ser Val Glu
    530                 535                 540

Arg Ile Tyr Glu Val Ser Phe Leu Pro Thr Glu Pro Gly Ile Leu Thr
545                 550                 555                 560

Cys Ile Ala Gln Asn Ile Ile Asp Gly Lys Glu Arg Arg Thr Leu Thr
                565                 570                 575

Lys Ala His Val Leu Leu Gly Asn Ile Ser Glu Asn Met Thr Ile Tyr
            580                 585                 590

Gly Phe Asp Lys Asp His Lys Ile Ala Lys Glu Asp Asn Val Asn Phe
        595                 600                 605

Thr Cys Glu Ala Leu Ala Tyr His Phe Asp Gly Asn Leu Lys Trp Phe
    610                 615                 620

Ile Asn Gly Glu Asp Leu Lys Glu Ser Asp Ser Val His Ile Glu Thr
625                 630                 635                 640

Ser His Thr Lys Tyr Ser Tyr Lys Ser Thr Val His Ile Thr Thr Ile
                645                 650                 655

Ser Asp Arg Asp Arg Gly Thr Tyr Glu Cys Arg Ala Tyr His Asn Asp
            660                 665                 670

Lys Asp Ala Val Tyr Ser Ser Arg Glu Ile Asp Leu Tyr Val His Asp
        675                 680                 685

Pro Ser Ala Pro Gln Trp Thr Asn Gly Gly Gln Glu Gly His Ser Lys
    690                 695                 700

Ile Lys Arg Lys Leu Ser Gln Thr Leu Glu Leu Glu Cys Ala Ser Thr
705                 710                 715                 720

Ala Val Pro Val Ala Ile Val Arg Trp Phe Lys Asp Asp Lys Glu Val
                725                 730                 735

Thr Glu Ser Lys Leu Arg His Ile Ile Glu Lys Glu Ser Lys Leu Leu
            740                 745                 750

Ile Thr His Leu Tyr Pro Gly Asp Glu Gly Val Tyr Lys Cys Val Val
        755                 760                 765

Glu Asn Arg Leu Asp Arg Ile Glu Arg Ser Phe Thr Val Val Ile Ser
    770                 775                 780

Asp Leu Pro Gly Ile Ser Met Ala Trp Val Trp Phe Gly Val Ile Leu
785                 790                 795                 800

Phe Leu Ile Leu Ile Gly Leu Cys Val Phe Leu Ala Val Arg Tyr Gln
                805                 810                 815

Lys Glu His Lys Arg His Leu Ala Leu Lys Ala Ala Gly Leu Ala Asn
            820                 825                 830

Phe Glu Glu Gly Ala Val Gly His Ile Asn Pro Asp Leu Thr Leu Asp
        835                 840                 845

Glu Gln Ala Glu Leu Leu Pro Tyr Asn Arg Glu Phe Glu Phe Pro Arg
    850                 855                 860

Glu Asn Leu Lys Leu Gly Lys Gln Leu Gly Ala Gly Ala Phe Gly Val
865                 870                 875                 880

Val Leu Lys Gly Glu Ala Lys Gly Ile Arg Arg Glu Glu Pro Thr Thr
                885                 890                 895

Thr Val Ala Val Lys Met Val Lys Ala Thr Ala Asp Asn Glu Val Val
            900                 905                 910

Arg Ala Leu Val Ser Glu Leu Lys Ile Met Val His Leu Gly Gln His
        915                 920                 925

Leu Asn Val Val Asn Leu Leu Gly Ala Val Thr Lys Asn Ile Ala Lys
```

-continued

```
    930                 935                 940

Arg Glu Leu Met Val Ile Val Glu Tyr Cys Arg Phe Gly Asn Ile Gln
945                 950                 955                 960

Asn Phe Leu Leu Arg Asn Arg Lys Cys Phe Ile Asn Gln Ile Asn Pro
                965                 970                 975

Asp Thr Asp His Ile Asp Pro Ser Ile Ile Thr Gln Arg Met Ser Asp
            980                 985                 990

Asn Tyr Glu Leu His Arg Asn Ser  Asp Asn Asp Pro Arg  Ser Gly Thr
        995                 1000                1005

Arg Ala  Gly Arg Thr Gly Ser  Gly Thr Ala Thr Tyr  Ser Tyr Asp
    1010                 1015                 1020

Arg Gln  Met Asp Thr Cys Ala  Thr Val Met Thr Thr  Val Pro Glu
    1025                 1030                 1035

Asp Asp  Gln Ile Met Ser Asn  Asn Ser Val Gln Pro  Ala Trp Arg
    1040                 1045                 1050

Ser Asn  Tyr Lys Thr Asp Ser  Thr Glu Ala Met Thr  Val Thr Thr
    1055                 1060                 1065

Val Asp  Leu Ile Ser Trp Ala  Phe Gln Val Ala Arg  Gly Met Asp
    1070                 1075                 1080

Tyr Leu  Ser Ser Lys Lys Val  Leu His Gly Asp Leu  Ala Ala Arg
    1085                 1090                 1095

Asn Ile  Leu Leu Cys Glu Asp  Asn Val Val Lys Ile  Cys Asp Phe
    1100                 1105                 1110

Gly Leu  Ala Arg Ser Met Tyr  Arg Gly Asp Asn Tyr  Lys Lys Ser
    1115                 1120                 1125

Glu Asn  Gly Lys Leu Pro Ile  Lys Trp Leu Ala Leu  Glu Ser Leu
    1130                 1135                 1140

Ser Asp  His Val Phe Ser Thr  Tyr Ser Asp Val Trp  Ser Tyr Gly
    1145                 1150                 1155

Ile Val  Leu Trp Glu Met Phe  Ser Leu Ala Lys Val  Pro Tyr Pro
    1160                 1165                 1170

Gly Ile  Asp Pro Asn Gln Glu  Leu Phe Asn Lys Leu  Asn Asp Gly
    1175                 1180                 1185

Tyr Arg  Met Glu Lys Pro Lys  Phe Ala Asn Gln Glu  Leu Tyr Glu
    1190                 1195                 1200

Ile Met  Leu Glu Cys Trp Arg  Lys Asn Pro Glu Ser  Arg Pro Leu
    1205                 1210                 1215

Phe Ala  Glu Leu Glu Lys Arg  Phe Ala Asn Met Leu  Gly Glu Asp
    1220                 1225                 1230

Val Ala  Ser His Cys Leu Asp  Leu Asn Asn Pro Tyr  Met Gln Ser
    1235                 1240                 1245

Asn Ile  Glu Tyr Met Lys Lys  Gln Ser Thr Asp Tyr  Leu Ala Leu
    1250                 1255                 1260

Met Gly  Ser Pro Asp Glu Leu  Ala Pro Ala Ala Pro  Arg Tyr Val
    1265                 1270                 1275

Asn Gly  His Ile Val Pro Asp  Ile Arg Ile Glu Glu  Leu Pro Asp
    1280                 1285                 1290

Asp Tyr  Met Glu Met Ser Arg  Asp Ser Asp Pro Asp  Ala Cys Thr
    1295                 1300                 1305

Ala Ile  Phe Ser Pro Thr Arg  Leu Glu Gly Glu Ser  Ser Asp Phe
    1310                 1315                 1320

Pro Asp  Phe Ser Ser Glu Thr  Thr Phe Asn Phe Pro  Gly Ala Arg
    1325                 1330                 1335
```

-continued

```
Gln Ser  Pro Thr Leu Ser Asn  Asn Leu Asn Ser Gly  Ser Ser Lys
    1340                 1345                 1350

Pro Leu  Arg Lys Lys Asn Gly  Met Pro Thr Val Asp  Val Ala Asp
    1355                 1360                 1365

Gln Ala  Pro Glu Glu Ile Pro  Met Leu His Arg Ser  Ser Thr Gly
    1370                 1375                 1380

Ser Asp  Gly Ser Pro Glu Gln  Gly Arg Arg Phe Asn  Gln Ala Leu
    1385                 1390                 1395

Lys Gln  Gln Tyr Val Thr Pro  Thr Pro Ser Pro Arg  His His Val
    1400                 1405                 1410

Glu Thr  Lys Leu Asn Gly Glu  Pro Ser Glu Asn Tyr  Val Asn Met
    1415                 1420                 1425

Lys Pro  Pro Arg Lys Asn Ile  Pro Gly Lys Thr Thr  Thr Gly Gly
    1430                 1435                 1440

Gly Gly  Ala Ala Ala Gly Ala  Ser Thr Glu Ala Phe  Ser Asn Pro
    1445                 1450                 1455

Ser Tyr  Gln Pro Leu Ser Thr  Val Asn Glu Lys Glu  Gln Arg Arg
    1460                 1465                 1470

Tyr
```

<210> SEQ ID NO 5
<211> LENGTH: 5170
<212> TYPE: DNA
<213> ORGANISM: Drosophila melanogaster

<400> SEQUENCE: 5

```
atggcgatgc ttccgcggtt gattctgctg ccactgctcc tgattttgcg gatctcgtgg     60

agcgatgctg tgcctttgca gcagttctca ccggatcccg atgacagcat cgagaactgc    120

ggcggcgaga atggagctcc cctgatgacg ccctgcaaga gcgccattat cctggatgcc    180

cagacgagca ccacgcttaa gtgcgaggac gacgagccga tgagctggtg gaccagtcaa    240

tcgcaatatg tgcatgtgaa gtccttcgat aatacggagg atccggctcg accattcgga    300

actagcctgc atctcatcga agtgacggct gactatgtgg cagcctacta ttgcgtgaag    360

acttcgaaat tcagtcagat cgccaaggag gagcagtcgg acgaggcgat gatcgaattg    420

gttaatcaag gatacgccag ctccatctac gtgtacgtga atgatccgga cactaagctg    480

gtcgatagtc ataacgtggt gacggcacgc cagtataccg acgtagtcat accctgtaaa    540

ccagccatgc cggacacaga ggtgctgcta gagaccagta atggagaaat gcattccagc    600

aaatctgtcg gtcgatacga tccgcaacgg ggattcacca tcgaaatccg aagcatcgtg    660

gatggcggag actactactg ccgacccaat ccgccattcc cgcataacga agaggagatg    720

accagcatag aagtgcgctt tattgaagac ggcaaaccgc tgccaaagcc cgtgatcagg    780

tcctccgtgg agcatcacgt cttcacggac accaacttca ccctggattg cgagcagtcc    840

gcctacgttg aatcagtata cggaatggaa tggttcactc cgtcccggga tgagaatcgc    900

atatttgcct cccaatcaag aaccgatccc aagaccagga acagcaccca tcagacgggc    960

aggagcacct tgacagtgct aaatgcacaa ccctcggaca ctggtctata caagtgtgtg   1020

acaacagata attctaacca gaacgtacaa cgtgccacct acaggattaa ggtgctaaag   1080

caaaacgaaa gttacctgaa cgtgggcgaa ccatcgggtc attacaacgt tcaggaatat   1140

gccaatcgca cgatccaaat gaccgcgaac tttgagggat ttccgacgcc ctccttcagt   1200

tggttcaaac ccgatggcac cgaggtgcga caatcggaga ataacttcaa gattctctcc   1260
```

-continued

```
acggaattga gcacaatgct ccaggtgctg aacgcccaat tgcaggacag cggcacgtat   1320
gtcctccgtg gatccaattc cttcggcgtc gttcagcggg agtacaacgt cagtgtgatg   1380
gacgcaccgg cgctgaagat gtcggacgcc tatgtccagg tgggatccgt ggcgcgactg   1440
gagtgcacag tacgctccta tccgccggct atcgtgacct tcttcttccg cccctgcagc   1500
ctggaaccac agtggcccac ttgctctgtg ctcaatcaga actttagctt gccgagtgaa   1560
caggagaaat atgagttcca gacccggccc agacccggaa agctgagtgt ggaacgcata   1620
tacgaggtat ccttcctgcc cacggagccg ggaatcctca catgcattgc ccaaaatatc   1680
attgatggaa aggaacgaag aaccctgacg aaggcgcacg ttctgctggg caacatttcc   1740
gagaacatga ccatatatgg cttcgataag gatcacaaaa tcgccaagga ggacaatgtg   1800
aacttcacct gcgaggcgct ggcctatcac ttcgatggaa atcttaaatg gttcatcaat   1860
ggagaggatt tgaaggagtc ggattcggtt cacattgaga ccagccatac caagtactcc   1920
tacaagagca ctgtacacat cacaacgata tccgacaggg atcgtggaac ctatgagtgc   1980
cgggcctacc acaacgacaa ggatgccgtt tacagcagcc gggagataga cttgtacgtc   2040
cacgatccct ctgctcctca gtggacaaac ggcggacagg agggtcactc gaaaataaag   2100
cgcaaactaa gccaaacgct ggagctggag tgtgcctcca cagcggttcc cgtggcaatt   2160
gtgcgttggt ttaaggacga caaggaagtg accgaatcaa agctcaggca catcattgaa   2220
aaggaatcca agctgctgat cactcacctg tatcccggag atgaaggcgt ctacaagtgt   2280
gtggtggaga accgattgga cagaatcgaa cgctccttca cggtagtgat atcagatctg   2340
cccggcatta gcatggcctg ggtgtggttc ggtgtgatac tattcctcat cctgatcggt   2400
ctgtgcgtct tcctcgccgt gcgctaccag aaggagcaca agcggcatct ggcccttaag   2460
gcagccggat tggccaactt cgaggagggc gccgtgggac acatcaatcc cgatctgacc   2520
ctggacgagc aggcggaact gctgccctac aatcgggaat tcgagttccc acgggaaaac   2580
ctgaaactgg gcaagcaact cggagccgga gcatttggcg ttgtgctcaa gggcgaggcc   2640
aagggcatcc ggcgagagga gcccaccacc acggtggccg tcaaaatggt caaggcgacg   2700
gctgacaacg aggtggtgcg ggcactggtc tccgagctca agatcatggt acatctggga   2760
cagcacttga atgtggtcaa tctcctgggt gcagttacca aaaatattgc gaagcgcgaa   2820
ctaatggtca ttgtggaata ctgtcgcttt ggcaacatac agaacttcct tctgaggaac   2880
agaaagtgct ttatcaatca aatcaatcca gacaccgatc acattgaccc cagcatcatg   2940
acccagcgca tgtccgacaa ctacgaactg caccgcgata cgaatggtgg tggcttgaag   3000
tacgccaatg tcggtttccc gatccactct tacattaatg agccgcacaa caataacacg   3060
caaccgccaa ctcatcgcag aaattcggac aatgatcccc gatcgggcac ccgagccgga   3120
cgaaccggat ccggaacagc cacctacagc tacgaccgtc agatggatac ctgtgccacc   3180
gtaatgacca ccgtcccaga agacgatcaa ataatgtcca ataactccgt acaacccgcc   3240
tggcgttcca attacaaaac cgactccacg gaggcgatga cagtgaccac tgtggatttg   3300
atcagttggg cattccaagt ggcaaggggc atggattact tgtcctccaa gaaggtgttg   3360
cacggcgatc tggccgctag aaatattctc ctctgcgagg acaatgtggt aaagatttgt   3420
gactttggtc tggctcgatc catgtatcga ggtgataact acaagaagtc agagaatggc   3480
aaattgccca tcaagtggct ggcgctggaa tcgctgagcg atcatgtgtt cagcacatac   3540
agcgatgttt ggtcctacgg aattgttcta tgggagatgt tctcgctggc caaggtgccg   3600
```

-continued

```
tatccgggca tcgatcccaa ccaagagcta tttaacaaac tgaacgatgg ctaccgcatg   3660

gagaagccga aatttgccaa ccaggagctc tacgagatta tgctagagtg ctggcgaaag   3720

aatcccgaga gcagaccttt gtttgctgag ctggagaagc gatttgcaaa catgctgggc   3780

gaggatgtag ccagccacta cctggaccta aacaatccgt acatgcagag caacattgag   3840

tacatgaaga agcagtctac ggattacctg gcactgatgg gatcacccga cgagctggcg   3900

cctgcagctc cgcgctacgt gaacgggcac atagtgcccg atatacgcat cgaagagctg   3960

ccggatgact acatggagat gagccgggat tctgatcccg atgcctgcac cgccatattc   4020

tcacccacac gcctcgaggg cgagtcctca gactttccgg atttctctag cgaaaccact   4080

ttcaatttcc caggggcgcg acagtcgcct acgctgagta acaatctcaa cagcggatcg   4140

agtaagccgc tccgcaagaa gaacggcatg ccaactgtgg atgtgccaga tcaggcgccg   4200

gaggagatac ctatgctgca tcgcagctcc actggatcgg atggaagtcc ggaacaggga   4260

aggcgcttca atcaggccct taagcagcag tatgtcacgc ccacaccgtc ccctcgccat   4320

catgtggaga ccaaactcaa tggggagcca tccgaaaact atgtgaatat gaagccaccc   4380

aggaagaata tacccggcaa aaccacaaca ggtggcgggg gtgctgctgc tggagcctcc   4440

acggaggcct tctcgaatcc cagctaccag ccactgtcca ccgtcaacga gaaggagcaa   4500

cgaaggtatt aggacgtccc ggagccatta gattaagttt aggacctctt tgcagctcag   4560

ttggagtttt aagtgaaatc ttaaatagaa aattttaaat attgtataat caacttatgt   4620

aatgactatt gttgatctta ggaaaacaaa ttgttaacag aaagtaatcg tacgcgatat   4680

aaccttttaa aaaaaagtta aaatttcaac ttaattgttt aggggccttt aagaaacaat   4740

actacttagt ggcattgtta agattctgat atagctttag gaccacacac tcactccatg   4800

ttatatacta ttaatgccat ttcatgtttt acatttagtg tagtctaagt cgattaaact   4860

tatctatgta aatgattgtc ttgaattgtg tatgcatgta cctacgacta ctcaaataca   4920

atgggtatga taacaataaa aaaaaaaaaa aaaaaaaaaa aaaaaaaaaa aaaaaaaaac   4980

tcgagggggg gcccggtacc caattcgccc tatagtgagt cgtattacaa ttcactggcc   5040

gtcgttttac aacgtcgtga ctgggaaaac cctggcgtta cccaacttaa tcgccttgca   5100

gcacatcccc ctttcgccag ctggcgtaat agcgaaaagg cccgcaccga tcgcccttcc   5160

caacagttgc                                                          5170
```

<210> SEQ ID NO 6
<211> LENGTH: 1503
<212> TYPE: PRT
<213> ORGANISM: Drosophila melanogaster

<400> SEQUENCE: 6

```
Met Ala Met Leu Pro Arg Leu Ile Leu Leu Pro Leu Leu Leu Ile Leu
1               5                   10                  15

Arg Ile Ser Trp Ser Asp Ala Val Pro Leu Gln Gln Phe Ser Pro Asp
            20                  25                  30

Pro Asp Asp Ser Ile Glu Asn Cys Gly Gly Glu Asn Gly Ala Pro Leu
        35                  40                  45

Met Thr Pro Cys Lys Ser Ala Ile Ile Leu Asp Ala Gln Thr Ser Thr
    50                  55                  60

Thr Leu Lys Cys Glu Asp Asp Glu Pro Met Ser Trp Trp Thr Ser Gln
65                  70                  75                  80

Ser Gln Tyr Val His Val Lys Ser Phe Asp Asn Thr Glu Asp Pro Ala
                85                  90                  95
```

-continued

```
Arg Pro Phe Gly Thr Ser Leu His Leu Ile Glu Val Thr Ala Asp Tyr
            100                 105                 110

Val Ala Ala Tyr Tyr Cys Val Lys Thr Ser Lys Phe Ser Gln Ile Ala
        115                 120                 125

Lys Glu Glu Gln Ser Asp Glu Ala Met Ile Glu Leu Val Asn Gln Gly
    130                 135                 140

Tyr Ala Ser Ser Ile Tyr Val Tyr Val Asn Asp Pro Asp Thr Lys Leu
145                 150                 155                 160

Val Asp Ser His Asn Val Val Thr Ala Arg Gln Tyr Thr Asp Val Val
                165                 170                 175

Ile Pro Cys Lys Pro Ala Met Pro Asp Thr Glu Val Leu Leu Glu Thr
            180                 185                 190

Ser Asn Gly Glu Met His Ser Ser Lys Ser Val Gly Arg Tyr Asp Pro
        195                 200                 205

Gln Arg Gly Phe Thr Ile Glu Ile Arg Ser Ile Val Asp Gly Gly Asp
    210                 215                 220

Tyr Tyr Cys Arg Pro Asn Pro Pro Phe Pro His Asn Glu Glu Glu Met
225                 230                 235                 240

Thr Ser Ile Glu Val Arg Phe Ile Glu Asp Gly Lys Pro Leu Pro Lys
                245                 250                 255

Pro Val Ile Arg Ser Ser Val Glu His His Val Phe Thr Asp Thr Asn
            260                 265                 270

Phe Thr Leu Asp Cys Glu Gln Ser Ala Tyr Val Glu Ser Val Tyr Gly
        275                 280                 285

Met Glu Trp Phe Thr Pro Ser Arg Asp Glu Asn Arg Ile Phe Ala Ser
    290                 295                 300

Gln Ser Arg Thr Asp Pro Lys Thr Arg Asn Ser Thr His Gln Thr Gly
305                 310                 315                 320

Arg Ser Thr Leu Thr Val Leu Asn Ala Gln Pro Ser Asp Thr Gly Leu
                325                 330                 335

Tyr Lys Cys Val Thr Thr Asp Asn Ser Asn Gln Asn Val Gln Arg Ala
            340                 345                 350

Thr Tyr Arg Ile Lys Val Leu Lys Gln Asn Glu Ser Tyr Leu Asn Val
        355                 360                 365

Gly Glu Pro Ser Gly His Tyr Asn Val Gln Glu Tyr Ala Asn Arg Thr
    370                 375                 380

Ile Gln Met Thr Ala Asn Phe Glu Gly Phe Pro Thr Pro Ser Phe Ser
385                 390                 395                 400

Trp Phe Lys Pro Asp Gly Thr Glu Val Arg Gln Ser Glu Asn Asn Phe
                405                 410                 415

Lys Ile Leu Ser Thr Glu Leu Ser Thr Met Leu Gln Val Leu Asn Ala
            420                 425                 430

Gln Leu Gln Asp Ser Gly Thr Tyr Val Leu Arg Gly Ser Asn Ser Phe
        435                 440                 445

Gly Val Val Gln Arg Glu Tyr Asn Val Ser Val Met Asp Ala Pro Ala
    450                 455                 460

Leu Lys Met Ser Asp Ala Tyr Val Gln Val Gly Ser Val Ala Arg Leu
465                 470                 475                 480

Glu Cys Thr Val Arg Ser Tyr Pro Pro Ala Ile Val Thr Phe Phe Phe
                485                 490                 495

Arg Pro Cys Ser Leu Glu Pro Gln Trp Pro Thr Cys Ser Val Leu Asn
            500                 505                 510
```

-continued

```
Gln Asn Phe Ser Leu Pro Ser Glu Gln Glu Lys Tyr Glu Phe Gln Thr
        515                 520                 525

Arg Pro Arg Pro Gly Lys Leu Ser Val Glu Arg Ile Tyr Glu Val Ser
    530                 535                 540

Phe Leu Pro Thr Glu Pro Gly Ile Leu Thr Cys Ile Ala Gln Asn Ile
545                 550                 555                 560

Ile Asp Gly Lys Glu Arg Arg Thr Leu Thr Lys Ala His Val Leu Leu
                565                 570                 575

Gly Asn Ile Ser Glu Asn Met Thr Ile Tyr Gly Phe Asp Lys Asp His
            580                 585                 590

Lys Ile Ala Lys Glu Asp Asn Val Asn Phe Thr Cys Glu Ala Leu Ala
        595                 600                 605

Tyr His Phe Asp Gly Asn Leu Lys Trp Phe Ile Asn Gly Glu Asp Leu
    610                 615                 620

Lys Glu Ser Asp Ser Val His Ile Glu Thr Ser His Thr Lys Tyr Ser
625                 630                 635                 640

Tyr Lys Ser Thr Val His Ile Thr Thr Ile Ser Asp Arg Asp Arg Gly
                645                 650                 655

Thr Tyr Glu Cys Arg Ala Tyr His Asn Asp Lys Asp Ala Val Tyr Ser
            660                 665                 670

Ser Arg Glu Ile Asp Leu Tyr Val His Asp Pro Ser Ala Pro Gln Trp
        675                 680                 685

Thr Asn Gly Gly Gln Glu Gly His Ser Lys Ile Lys Arg Lys Leu Ser
    690                 695                 700

Gln Thr Leu Glu Leu Glu Cys Ala Ser Thr Ala Val Pro Val Ala Ile
705                 710                 715                 720

Val Arg Trp Phe Lys Asp Asp Lys Glu Val Thr Glu Ser Lys Leu Arg
                725                 730                 735

His Ile Ile Glu Lys Glu Ser Lys Leu Leu Ile Thr His Leu Tyr Pro
            740                 745                 750

Gly Asp Glu Gly Val Tyr Lys Cys Val Val Glu Asn Arg Leu Asp Arg
        755                 760                 765

Ile Glu Arg Ser Phe Thr Val Val Ile Ser Asp Leu Pro Gly Ile Ser
    770                 775                 780

Met Ala Trp Val Trp Phe Gly Val Ile Leu Phe Leu Ile Leu Ile Gly
785                 790                 795                 800

Leu Cys Val Phe Leu Ala Val Arg Tyr Gln Lys Glu His Lys Arg His
                805                 810                 815

Leu Ala Leu Lys Ala Ala Gly Leu Ala Asn Phe Glu Glu Gly Ala Val
            820                 825                 830

Gly His Ile Asn Pro Asp Leu Thr Leu Asp Glu Gln Ala Glu Leu Leu
        835                 840                 845

Pro Tyr Asn Arg Glu Phe Glu Phe Pro Arg Glu Asn Leu Lys Leu Gly
    850                 855                 860

Lys Gln Leu Gly Ala Gly Ala Phe Gly Val Val Leu Lys Gly Glu Ala
865                 870                 875                 880

Lys Gly Ile Arg Arg Glu Glu Pro Thr Thr Thr Val Ala Val Lys Met
                885                 890                 895

Val Lys Ala Thr Ala Asp Asn Glu Val Val Arg Ala Leu Val Ser Glu
            900                 905                 910

Leu Lys Ile Met Val His Leu Gly Gln His Leu Asn Val Val Asn Leu
        915                 920                 925

Leu Gly Ala Val Thr Lys Asn Ile Ala Lys Arg Glu Leu Met Val Ile
```

-continued

```
    930                 935                 940

Val Glu Tyr Cys Arg Phe Gly Asn Ile Gln Asn Phe Leu Leu Arg Asn
945                 950                 955                 960

Arg Lys Cys Phe Ile Asn Gln Ile Asn Pro Asp Thr Asp His Ile Asp
                965                 970                 975

Pro Ser Ile Met Thr Gln Arg Met Ser Asp Asn Tyr Glu Leu His Arg
            980                 985                 990

Asp Thr Asn Gly Gly Gly Leu Lys  Tyr Ala Asn Val Gly  Phe Pro Ile
        995                 1000                1005

His Ser  Tyr Ile Asn Glu Pro  His Asn Asn Asn Thr  Gln Pro Pro
    1010                 1015                 1020

Thr His  Arg Arg Asn Ser Asp  Asn Asp Pro Arg Ser  Gly Thr Arg
    1025                 1030                 1035

Ala Gly  Arg Thr Gly Ser Gly  Thr Ala Thr Tyr Ser  Tyr Asp Arg
    1040                 1045                 1050

Gln Met  Asp Thr Cys Ala Thr  Val Met Thr Thr Val  Pro Glu Asp
    1055                 1060                 1065

Asp Gln  Ile Met Ser Asn Asn  Ser Val Gln Pro Ala  Trp Arg Ser
    1070                 1075                 1080

Asn Tyr  Lys Thr Asp Ser Thr  Glu Ala Met Thr Val  Thr Thr Val
    1085                 1090                 1095

Asp Leu  Ile Ser Trp Ala Phe  Gln Val Ala Arg Gly  Met Asp Tyr
    1100                 1105                 1110

Leu Ser  Ser Lys Lys Val Leu  His Gly Asp Leu Ala  Ala Arg Asn
    1115                 1120                 1125

Ile Leu  Leu Cys Glu Asp Asn  Val Val Lys Ile Cys  Asp Phe Gly
    1130                 1135                 1140

Leu Ala  Arg Ser Met Tyr Arg  Gly Asp Asn Tyr Lys  Lys Ser Glu
    1145                 1150                 1155

Asn Gly  Lys Leu Pro Ile Lys  Trp Leu Ala Leu Glu  Ser Leu Ser
    1160                 1165                 1170

Asp His  Val Phe Ser Thr Tyr  Ser Asp Val Trp Ser  Tyr Gly Ile
    1175                 1180                 1185

Val Leu  Trp Glu Met Phe Ser  Leu Ala Lys Val Pro  Tyr Pro Gly
    1190                 1195                 1200

Ile Asp  Pro Asn Gln Glu Leu  Phe Asn Lys Leu Asn  Asp Gly Tyr
    1205                 1210                 1215

Arg Met  Glu Lys Pro Lys Phe  Ala Asn Gln Glu Leu  Tyr Glu Ile
    1220                 1225                 1230

Met Leu  Glu Cys Trp Arg Lys  Asn Pro Glu Ser Arg  Pro Leu Phe
    1235                 1240                 1245

Ala Glu  Leu Glu Lys Arg Phe  Ala Asn Met Leu Gly  Glu Asp Val
    1250                 1255                 1260

Ala Ser  His Tyr Leu Asp Leu  Asn Asn Pro Tyr Met  Gln Ser Asn
    1265                 1270                 1275

Ile Glu  Tyr Met Lys Lys Gln  Ser Thr Asp Tyr Leu  Ala Leu Met
    1280                 1285                 1290

Gly Ser  Pro Asp Glu Leu Ala  Pro Ala Ala Pro Arg  Tyr Val Asn
    1295                 1300                 1305

Gly His  Ile Val Pro Asp Ile  Arg Ile Glu Glu Leu  Pro Asp Asp
    1310                 1315                 1320

Tyr Met  Glu Met Ser Arg Asp  Ser Asp Pro Asp Ala  Cys Thr Ala
    1325                 1330                 1335
```

-continued

```
Ile Phe  Ser Pro Thr Arg Leu  Glu Gly Glu Ser Ser  Asp Phe Pro
    1340                 1345                 1350

Asp Phe  Ser Ser Glu Thr Thr  Phe Asn Phe Pro Gly  Ala Arg Gln
    1355                 1360                 1365

Ser Pro  Thr Leu Ser Asn Asn  Leu Asn Ser Gly Ser  Ser Lys Pro
    1370                 1375                 1380

Leu Arg  Lys Lys Asn Gly Met  Pro Thr Val Asp Val  Pro Asp Gln
    1385                 1390                 1395

Ala Pro  Glu Glu Ile Pro Met  Leu His Arg Ser Ser  Thr Gly Ser
    1400                 1405                 1410

Asp Gly  Ser Pro Glu Gln Gly  Arg Arg Phe Asn Gln  Ala Leu Lys
    1415                 1420                 1425

Gln Gln  Tyr Val Thr Pro Thr  Pro Ser Pro Arg His  His Val Glu
    1430                 1435                 1440

Thr Lys  Leu Asn Gly Glu Pro  Ser Glu Asn Tyr Val  Asn Met Lys
    1445                 1450                 1455

Pro Pro  Arg Lys Asn Ile Pro  Gly Lys Thr Thr Thr  Gly Gly Gly
    1460                 1465                 1470

Gly Ala  Ala Ala Gly Ala Ser  Thr Glu Ala Phe Ser  Asn Pro Ser
    1475                 1480                 1485

Tyr Gln  Pro Leu Ser Thr Val  Asn Glu Lys Glu Gln  Arg Arg Tyr
    1490                 1495                 1500
```

<210> SEQ ID NO 7
<211> LENGTH: 4943
<212> TYPE: DNA
<213> ORGANISM: Drosophila melanogaster
<220> FEATURE:
<221> NAME/KEY: misc_feature
<223> OTHER INFORMATION: "n" is A, C, G, or T

<400> SEQUENCE: 7

```
atggcgatgc ttccgcggtt gattctgctg ccactgctcc tgattttgcg gatctcgtgg     60

agcgatgctg tgcctttgca gcagttctca ccggatcccg atgacagcat cgagaactgc    120

ggcggcgaga atggagctcc cctgatgacg ccctgcaaga gcgccattat cctggatgcc    180

cagacgagca ccacgcttaa gtgcgaggac gacgagccga tgagctggtg gaccagtcaa    240

tcgcaatatg tgcatgtgaa gtccttcgat aatacggagg atccggctcg accattcgga    300

actagcctgc atctcatcga agtgacggct gactatgtgg cagcctacta ttgcgtgaag    360

acttcgaaat tcagtcagat cgccaaggag gagcagtcgg acgaggcgat gatcgaattg    420

gttaatcaag gatacgccag ctccatctac gtgtacgtga atgatccgga cactaagctg    480

gtcgatagtc ataacgtggt gacggcacgc cagtataccg acgtagtcat accctgtaaa    540

ccagccatgc cggacacaga ggtgctgcta gagaccagta atggagaaat gcattccagc    600

aaatctgtcg gtcgatacga tccgcaacgg ggattcacca tcgaaatccg aagcatcgtg    660

gatggcggag actactactg ccgacccaat ccgccattcc cgcataacga agaggagatg    720

accagcatag aaaagacggc aaaccgctgc caaagcccgt gatcaggtcc tccgtggagc    780

atcacgtctt cacggacacc aacttcaccc tggattgcga gcagtccgcc tacgttgaat    840

cagtatacgg aatggaatgg ttcactccgt cccgggatga gaatcgcata tttgcctccc    900

aatcaagaac cgatcccaag accaggaaca gcacccatca gacgggcagg agcaccttga    960

cagtgctaaa tgcacaaccc tcggacactg gtctatacaa gtgtgtgaca acagataatt   1020
```

-continued

```
ctaaccagaa cgtacaacgt gccacctaca ggattaaggt gctaaagcaa aacgaaagtt   1080
acctgaacgt gggcgaacca tcgggtcatt acaacgttca ggaatatgcc aatcgcacga   1140
tccaaatgac cgcgaacttt gagggatttc cgacgccctc cttcagttgg ttcaaacccg   1200
atggcaccga ggtgcgacaa tcggagaata acttcaagat tctctccacg gaattgagca   1260
caatgctcca ggtgctgaac gcccaattgc aggacagcgg cacgtatgtc ctccgtggat   1320
ccaattcctt cggcgtcgtt cagcgggagt acaacgtcag tgtgatggac gcaccggcgc   1380
tgaagatgtc ggacgcctat gtccaggtgg gatccgtggc gcgactggag tgcacagtac   1440
gctcctatcc gccggctatc gtgaccttct tcttccgccc ctgcagcctg gaaccacagt   1500
ggcccacttg ctctgtgctc aatcagaact ttagcttgcc gagtgaacag gagaaatatc   1560
agttccagac ccggcccaga cccggaaagc tgagtgtgga acgcatatac gaggtatcct   1620
tcctgcccac ggagccggga atcctcacat gcattgccca aaatatcatt gatggaaagg   1680
aacgaagaac cctgacgaag gcgcacgttc tgctgggcaa catttccgag aacatgacca   1740
tatatggctt cgataaggat cacaaaatcg ccaaggagga caatgtgaac ttcacctgcg   1800
aggcgctggc ctatcacttc gatggaaatc ttaaatggtt catcaatgga gaggatttga   1860
aggagtcgga ttcggttcac attgagacca gccataccaa gtactcctac aagagcactg   1920
tacacatcac aacgatatcc gacagggatc gtggaaccta tgagtgccgg gcctaccaca   1980
acgacaagga tgccgtttac agcagccggg agatagactt gtacgtccac gatccctctg   2040
ctcctcagtg gacaaacggc ggacaggagg gtcactcgaa aataaagcgc aaactaagcc   2100
aaacgctgga gctggagtgt gcctccacag cggttcccgt ggcaattgtg cgttggttta   2160
aggacgacaa ggaagtgacc gaatcaaagc tcaggcacat cattgaaaag gaatccaagc   2220
tgctgatcac tcacctgtat cccggagatg aaggcgtcta caagtgtgtg gtggagaacc   2280
gattggacag aatcgaacgc tccttcacgg tagtgatatc agatctgccc ggcattagca   2340
tggcctgggt gtggttcggt gtgatactat tcctcatcct gatcggtctg tgcgtcttcc   2400
tcgccgtgcg ctaccagaag gagcacaagc ggcatctggc ccttaaggca gccggattgg   2460
ccaacttcga ggagggcgcc gtgggacaca tcaatcccga tctgaccctg gacgagcagg   2520
cggaactgct gccctacaat cgggaattcg agttcccacg ggaaaacctg aaactgggca   2580
agcaactcgg agccggagca tttggcgttg tgctcaaggg cgaggccaag ggcatccggc   2640
gagaggagcc caccaccacg gtggccgtca aaatggtcaa ggcgacggct gacaacgagg   2700
tggtgcgggc actggtctcc gagctcaaga tcatggtaca tctgggacag cacttgaatg   2760
tggtcaatct cctgggtgca gttaccaaaa atattgcgaa gcgcgaacta atggtcattg   2820
tggaatactg tcgctttggc aacatacaga acttccttct gaggaacaga aagtgcttta   2880
tcaatcaaat caatccagac accgatcaca ttgaccccag catcatgacc cagcgcatgt   2940
ccgacaacta cgaactgcac cgcgatacga atggtggtgg cttgaagtac gccaatgtcg   3000
gtttcccgat ccactcttac attaatgagc cgcacaacaa taacacgcaa ccgccaactc   3060
atcgcagaaa ttcggacaat gatccccgat cgggcacccg agccggacga accggatccg   3120
gaacagccac ctacagctac gaccgtcaga tggatacctg tgccaccgta atgaccaccg   3180
tcccagaaga cgatcaaata atgtccaata actccgtaca acccgcctgg cgttccaatt   3240
acaaaaccga ctccacggag gcgatgacag tgaccactgt ggatttgatc agttgggcat   3300
tccaagtggc aaggggcatg gattacttgt cctccaagaa ggtgttgcac ggcgatctgg   3360
ccgctagaaa tattctcctc tgcgaggaca atgtggtaaa gatttgtgac tttggtctgg   3420
```

-continued

```
ctcgatccat gtatcgaggt gataactaca agaagtcaga gaatggcaaa ttgcccatca   3480

agtggctggc gctggaatcg ctgagcgatc atgtgttcag cacatacagc gatgtttggt   3540

cctacggaat tgttctatgg gagatgttct cgctggccaa ggtgccgtat ccgggcatcg   3600

atcccaacca agagctattt aacaaactga acgatggcta ccgcatggag aagccgaaat   3660

ttgccaacca ggagctctac gagattatgc tagagtgctg gcgaaagaat cccgagagca   3720

gacctttgtt tgctgagctg gagaagcgat ttgcaaacat gctgggcgag gatgtagcca   3780

gccactacct ggacctaaac aatccgtaca tgcagagcaa cattgagtac atgaagaagc   3840

agtctacgga ttacctggca ctgatgggat cacccgacga gctggcgcct gcagctccgc   3900

gctacgtgaa cgggcacata gtgcccgata tacgcatcga agagctgccg gatgactaca   3960

tggagatgag ccgggattct gatcccgatg cctgcaccgc catattctca cccacacgcc   4020

tcgagggcga gtcctcagac tttccggatt tctctagcga aaccactttc aatttcccag   4080

gggcgcgaca gtcgcctacg ctgagtaaca atctcaacag cggatcgagt aagccgctcc   4140

gcaagaagaa cggcatgcca actgtggatg tggcagatca ggcgccggag gagataccta   4200

tgctgcatcg cagctccact ggatcggatg gaagtccgga acagggaagg cgcttcaatc   4260

aggcccttaa gcagcagtat gtcacgccca caccgtcccc tcgccatcat gtggagacca   4320

aactcaatgg ggagccatcc gaaaactatg tgaatatgaa gccacccagg aagaatatac   4380

ccggcaaaac cacaacaggt ggcgggggtg ctgctgctgg agcctccacg gaggccttct   4440

cgaatcccag ctaccagcca ctgtccaccg tcaacgagaa ggagcaacga aggtattagg   4500

acgtcccgga gccattagat taagtttagg acctctttgc agctcagttg gagttttaag   4560

tgaaatctta aatagaaaat tttaaatatt gtataatcaa cttatgtaat gactattgtt   4620

gatcttagga aaacaaattg ttaacagaaa gtaatcgtac gcgatataac cttttaaaaa   4680

aaagttaaaa tttcaactta attgtttagg ggcctttaag aaacaatact acttagtggc   4740

attgttaaga ttctgatata gctttaggac cacacactca ctccatgtta tatactatta   4800

atgccatttc atgttttaca tttagtgtag tctaagtcga ttaaacttat ctatgtaaat   4860

gattgtcttg aattgtgtat gcatgtacct acgactactc aaatacaatg ggtatgataa   4920

caatnaaaaa aaaaaaaaaa aaa                                             4943
```

<210> SEQ ID NO 8
<211> LENGTH: 253
<212> TYPE: PRT
<213> ORGANISM: Drosophila melanogaster

<400> SEQUENCE: 8

```
Met Ala Met Leu Pro Arg Leu Ile Leu Leu Pro Leu Leu Leu Ile Leu
1               5                   10                  15

Arg Ile Ser Trp Ser Asp Ala Val Pro Leu Gln Gln Phe Ser Pro Asp
            20                  25                  30

Pro Asp Asp Ser Ile Glu Asn Cys Gly Gly Glu Asn Gly Ala Pro Leu
        35                  40                  45

Met Thr Pro Cys Lys Ser Ala Ile Ile Leu Asp Ala Gln Thr Ser Thr
    50                  55                  60

Thr Leu Lys Cys Glu Asp Asp Glu Pro Met Ser Trp Trp Thr Ser Gln
65                  70                  75                  80

Ser Gln Tyr Val His Val Lys Ser Phe Asp Asn Thr Glu Asp Pro Ala
                85                  90                  95
```

-continued

| | | | | | | | | | | | | | | | |
|---|---|---|---|---|---|---|---|---|---|---|---|---|---|---|---|
| Arg | Pro | Phe | Gly | Thr | Ser | Leu | His | Leu | Ile | Glu | Val | Thr | Ala | Asp | Tyr |
| | | | 100 | | | | | 105 | | | | | 110 | | |
| Val | Ala | Ala | Tyr | Tyr | Cys | Val | Lys | Thr | Ser | Lys | Phe | Ser | Gln | Ile | Ala |
| | | 115 | | | | | 120 | | | | | 125 | | | |
| Lys | Glu | Glu | Gln | Ser | Asp | Glu | Ala | Met | Ile | Glu | Leu | Val | Asn | Gln | Gly |
| | 130 | | | | | 135 | | | | | 140 | | | | |
| Tyr | Ala | Ser | Ser | Ile | Tyr | Val | Tyr | Val | Asn | Asp | Pro | Asp | Thr | Lys | Leu |
| 145 | | | | | 150 | | | | | 155 | | | | | 160 |
| Val | Asp | Ser | His | Asn | Val | Val | Thr | Ala | Arg | Gln | Tyr | Thr | Asp | Val | Val |
| | | | | 165 | | | | | 170 | | | | | 175 | |
| Ile | Pro | Cys | Lys | Pro | Ala | Met | Pro | Asp | Thr | Glu | Val | Leu | Leu | Glu | Thr |
| | | | 180 | | | | | 185 | | | | | 190 | | |
| Ser | Asn | Gly | Glu | Met | His | Ser | Ser | Lys | Ser | Val | Gly | Arg | Tyr | Asp | Pro |
| | | 195 | | | | | 200 | | | | | 205 | | | |
| Gln | Arg | Gly | Phe | Thr | Ile | Glu | Ile | Arg | Ser | Ile | Val | Asp | Gly | Gly | Asp |
| | 210 | | | | | 215 | | | | | 220 | | | | |
| Tyr | Tyr | Cys | Arg | Pro | Asn | Pro | Pro | Phe | Pro | His | Asn | Glu | Glu | Glu | Met |
| 225 | | | | | 230 | | | | | 235 | | | | | 240 |
| Thr | Ser | Ile | Glu | Lys | Thr | Ala | Asn | Arg | Cys | Gln | Ser | Pro | | | |
| | | | | 245 | | | | | 250 | | | | | | |